US011322225B2

(12) United States Patent
Frey et al.

(10) Patent No.: US 11,322,225 B2
(45) Date of Patent: May 3, 2022

(54) SYSTEMS AND METHODS FOR DETERMINING EFFECTS OF THERAPIES AND GENETIC VARIATION ON POLYADENYLATION SITE SELECTION

(71) Applicant: Deep Genomics Incorporated, Toronto (CA)

(72) Inventors: Brendan Frey, Toronto (CA); Michael Ka Kit Leung, Markham (CA)

(73) Assignee: Deep Genomics Incorporated, Toronto (CA)

(*) Notice: Subject to any disclaimer, the term of this patent is extended or adjusted under 35 U.S.C. 154(b) by 0 days.

(21) Appl. No.: 17/162,224

(22) Filed: Jan. 29, 2021

(65) Prior Publication Data
US 2021/0241852 A1 Aug. 5, 2021

Related U.S. Application Data

(63) Continuation of application No. PCT/CA2019/051086, filed on Aug. 8, 2019.
(Continued)

(51) Int. Cl.
*G01N 33/48* (2006.01)
*G01N 33/50* (2006.01)
(Continued)

(52) U.S. Cl.
CPC ............ *G16B 25/00* (2019.02); *C12N 15/113* (2013.01); *C12Q 1/6869* (2013.01); *G06N 3/008* (2013.01);
(Continued)

(58) Field of Classification Search
CPC ........ G16B 25/00; G16B 30/00; G16B 20/20; G16B 40/00; G06N 20/00; G06N 3/008;
(Continued)

(56) References Cited

U.S. PATENT DOCUMENTS

| 2003/0224514 A1* | 12/2003 | Gaarde | C12N 15/1138 |
| | | | 435/375 |
| 2011/0239315 A1* | 9/2011 | Bonas | C12Q 1/6816 |
| | | | 800/13 |
| 2016/0364522 A1* | 12/2016 | Frey | G16B 40/20 |

FOREIGN PATENT DOCUMENTS

| WO | WO-2015089351 A1 | 6/2015 | |
| WO | WO-2016201564 A1 * | 12/2016 | G06N 3/04 |

(Continued)

OTHER PUBLICATIONS

Abadi, et al. Tensorflow: Large-scale machine learning on heterogeneous distributed systems. arXiv preprint arXiv:1603.04467 (2016).
(Continued)

*Primary Examiner* — Russell S Negin
(74) *Attorney, Agent, or Firm* — Wilson Sonsini Goodrich & Rosati

(57) ABSTRACT

The present disclosure provides systems and methods for determining effects of genetic variants on selection of polyadenylation sites (PAS) during polyadenylation processes. In an aspect, the present disclosure provides a polyadenylation code, a computational model that can predict alternative polyadenylation patterns from transcript sequences. A score can be calculated that describes or corresponds to the strength of a PAS, or the efficiency in which it is recognized by the 3'-end processing machinery. The polyadenylation model may be used, for example, to assess the effects of anti-sense oligonucleotides to alter transcript abundance. As another example, the polyadenylation model may be used to scan the 3'-UTR of a human genome to find potential PAS.

30 Claims, 11 Drawing Sheets

Specification includes a Sequence Listing.

Related U.S. Application Data

(60) Provisional application No. 62/716,262, filed on Aug. 8, 2018.

(51) Int. Cl.

| | |
|---|---|
| *G16B 25/00* | (2019.01) |
| *G06N 20/00* | (2019.01) |
| *G16B 20/20* | (2019.01) |
| *G16B 40/00* | (2019.01) |
| *G16B 30/00* | (2019.01) |
| *C12N 15/113* | (2010.01) |
| *C12Q 1/6869* | (2018.01) |
| *G06N 3/00* | (2006.01) |

(52) U.S. Cl.
CPC ............. *G06N 20/00* (2019.01); *G16B 20/20* (2019.02); *G16B 30/00* (2019.02); *G16B 40/00* (2019.02); *C12N 2310/11* (2013.01); *C12N 2830/50* (2013.01)

(58) Field of Classification Search
CPC ................ C12Q 1/6869; C12N 15/113; C12N 2310/11; C12N 2830/50
See application file for complete search history.

(56) References Cited

FOREIGN PATENT DOCUMENTS

| WO | WO-2017050836 A1 | 3/2017 |
|---|---|---|
| WO | WO-2017218925 A1 | 12/2017 |
| WO | WO-2020028989 A1 | 2/2020 |

OTHER PUBLICATIONS

Alipanahi, et al. Predicting the sequence specificities of DNA-and RNA-binding proteins by deep learning. Nature biotechnology 33.8 (2015): 831-838.
Beaudoing, et al. Patterns of variant polyadenylation signal usage in human genes. Genome research 10.7 (2000): 1001-1010.
Blanchette, et al. Aligning multiple genomic sequences with the threaded blockset aligner. Genome research 14.4 (2004): 708-715.
Cheng, et al. Prediction of mRNA polyadenylation sites by support vector machine. Bioinformatics 22.19 (2006): 2320-2325.
Cooper, et al. Distribution and intensity of constraint in mammalian genomic sequence. Genome research 15.7 (2005): 901-913.
Derti, et al. A quantitative atlas of polyadenylation in five mammals. Genome research 22.6 (2012): 1173-1183.
Glorot, et al. Understanding the difficulty of training deep feedforward neural networks. Proceedings of the thirteenth international conference on artificial intelligence and statistics. JMLR Workshop and Conference Proceedings, 2010.
Hafez, et al. Genome-wide identification and predictive modeling of tissue-specific alternative polyadenylation. Bioinformatics 29.13 (2013): i108-i116.
Harrow, et al. GENCODE: the reference human genome annotation for The ENCODE Project. Genome research 22.9 (2012): 1760-1774.
Hinton, et al. Improving neural networks by preventing co-adaptation of feature detectors. arXiv preprint arXiv:1207.0580 (2012).
Hu, et al. Bioinformatic identification of candidate cis-regulatory elements involved in human mRNA polyadenylation. Rna 11.10 (2005): 1485-1493.
Kaneko, et al. The Mammalian RNA Polymerase II C-Terminal Domain Interacts with RNA to Suppress Transcription-Coupled 3' End Formation, Mol. Cell., 2005.
Kent, et al. The human genome browser at UCSC. Genome research 12.6 (2002): 996-1006.
Kircher, et al. A general framework for estimating the relative pathogenicity of human genetic variants. Nature genetics 46.3 (2014): 310-315.
Landrum, et al. ClinVar: public archive of relationships among sequence variation and human phenotype. Nucleic acids research 42.D1 (2014): D980-D985.
Lee, et al. PolyA_DB 2: mRNA polyadenylation sites in vertebrate genes. Nucleic acids research 35.suppl_1 (2007): D165-D168.
Leung, et al. Deep learning of the tissue-regulated splicing code. Bioinformatics 30.12 (2014): i121-i129.
Leung, et al. Machine learning in genomic medicine: a review of computational problems and data sets. Proceedings of the IEEE 104.1 (2015): 176-197.
Lianoglou, et al. Ubiquitously transcribed genes use alternative polyadenylation to achieve tissue-specific expression. Genes & development 27.21 (2013): 2380-2396.
Macdonald, et al. Tissue-specific mechanisms of alternative polyadenylation: testis, brain, and beyond. Wiley Interdisciplinary Reviews: RNA 1.3 (2010): 494-501.
Muller, et al. APADB: a database for alternative polyadenylation and microRNA regulation events. Database 2014 (2014).
Ni, et al. Distinct polyadenylation landscapes of diverse human tissues revealed by a modified PA-seq strategy. BMC genomics 14.1 (2013): 1-15.
PCT/CA2019/051086 International Search Report dated Oct. 3, 2019.
Pollard, et al. Detection of nonneutral substitution rates on mammalian phylogenies. Genome research 20.1 (2010): 110-121.
Pruitt, et al. NCBI Reference Sequence (RefSeq): a curated non-redundant sequence database of genomes, transcripts and proteins. Nucleic acids research 33.suppl_1 (2005): D501-D504.
Rampasek, et al. TensorFlow: biology's gateway to deep learning?. Cell systems 2.1 (2016): 12-14.
Rund, et al. Two mutations in the beta-globin polyadenylylation signal reveal extended transcripts and new RNA polyadenylylation sites. Proceedings of the National Academy of Sciences 89.10 (1992): 4324-4328.
Siepel, et al. Evolutionarily conserved elements in vertebrate, insect, worm, and yeast genomes. Genome research 15.8 (2005): 1034-1050.
Simonyan, et al. Deep inside convolutional networks: Visualising image classification models and saliency maps.arXiv preprint arXiv:1312.6034 (2013).
Tian, et al. A large-scale analysis of mRNA polyadenylation of human and mouse genes. Nucleic acids research 33.1 (2005): 201-212.
Van Der Heijden, et al. Sequence-based prediction of single nucleosome positioning and genome-wide nucleosome occupancy. Proceedings of the National Academy of Sciences 109.38 (2012): E2514-E2522.
Vickers, et al. Fully modified 2' MOE oligonucleotides redirect polyadenylation. Nucleic acids research 29.6 (2001): 1293-1299.
Weng, et al. Poly (A) code analyses reveal key determinants for tissue-specific mRNA alternative polyadenylation. RNA 22.6 (2016): 813-821.
Xiong, et al. Probabilistic estimation of short sequence expression using RNA-Seq data and the "positional bootstrap". bioRxiv (2016): 046474.
Xiong, et al. The human splicing code reveals new insights into the genetic determinants of disease. Science DOI: 10.1126/ science. 1254806. Published Online Dec. 18, 2014.
Yates, et al. Ensembl 2016. Nucleic acids research 44.D1 (2016): D710-D716.
Zhang, et al. PolyA_DB: a database for mammalian mRNA polyadenylation. Nucleic acids research 33.suppl_1 (2005): D116-D120.

\* cited by examiner

SYSTEMS AND METHODS FOR DETERMINING EFFECTS OF THERAPIES AND GENETIC VARIATION ON POLYADENYLATION SITE SELECTION

CROSS-REFERENCE

This application is a continuation application of International Patent Application No. PCT/CA2019/051086, filed Aug. 8, 2019, which claims the benefit of U.S. Provisional Patent Application No. 62/716,262, filed Aug. 8, 2018, each of which is entirely incorporated by reference herein.

SEQUENCE LISTING

The instant application contains a Sequence Listing which has been submitted electronically in ASCII format and is incorporated by reference herein in its entirety. Said ASCII copy, created on Apr. 20, 2021, is named 51110-709_301_SL.txt and is 2,351 bytes in size.

BACKGROUND

Polyadenylation may be a mechanism responsible for regulating messenger ribonucleic acid (mRNA) function, stability, localization, and translation efficiency. As much as 70% of human genes may be subject to alternative polyadenylation (APA), and various mechanisms may influence its regulation. By selecting which polyadenylation site (PAS) among a plurality of possible polyadenylation sites is cleaved, different transcript (or mRNA) isoforms that may vary either in their coding sequences or in their 3' untranslated region (3'-UTR) can be produced. Transcripts differentially cleaved can influence how they are regulated.

SUMMARY

The recent availability of datasets profiling the selection of polyadenylation sites from across the genome and in different cell lines, tissues, and disease states, has made it possible to use machine learning to build systems that can ascertain the effects of genetic variation and genetically defined therapies, such as oligonucleotide therapies, gene editing and gene therapies, on polyadenylation site selection. This disclosure generally relates to a model of polyadenylation site selection.

In an aspect, the present disclosure provides a method for determining an effect of an antisense oligonucleotide on a plurality of candidate polyadenylation sites, the method comprising: (a) providing a plurality of genomic sequences, wherein the plurality of genomic sequences comprises (1) a reference sequence and (2) a variant sequence obtained by computer processing the reference sequence based on the antisense oligonucleotide, wherein the antisense oligonucleotide is complementary to at least a portion of the reference sequence; (b) for each of the plurality of genomic sequences: identifying a plurality of candidate polyadenylation sites in the genomic sequence; extracting a polyadenylation feature vector for each of the plurality of candidate polyadenylation sites, wherein each of the polyadenylation feature vectors comprises one or more features determined at least based on one or more nucleotides in the genomic sequence; and applying a trained algorithm to the plurality of polyadenylation feature vectors to calculate a set of preferences $p_1, p_2, \ldots, p_n$ for the plurality of candidate polyadenylation sites; and (c) computer processing the plurality of sets of preferences for each of the plurality of genomic sequences with each other to determine the effect of the antisense oligonucleotide.

In some embodiments, calculating the set of preferences for each of the plurality of genomic sequences comprises, for each of the plurality of candidate polyadenylation sites, computer processing by a first computation module the plurality of polyadenylation feature vectors of the genomic sequence to calculate an intermediate representation $r_i$ for an ith candidate polyadenylation site, the intermediate representation comprising at least one numerical value; and computer processing by a second computation module the set of intermediate representations $r_1, r_2, \ldots, r_n$ for the plurality of candidate polyadenylation sites to calculate the set of preferences $p_1, p_2, \ldots, p_n$ corresponding to the plurality of candidate polyadenylation sites. In some embodiments, the reference sequence is (i) derived from a human genome, (ii) obtained by sequencing deoxyribonucleic acid (DNA) or ribonucleic acid (RNA) of a bodily sample obtained from a subject, or (iii) a genetic aberration thereof. In some embodiments, the genetic aberration comprises a single nucleotide variant (SNV) or an insertion or deletion (indel). In some embodiments, at least one of the plurality of polyadenylation feature vectors comprises a feature determined at least based on one or more nucleotides in the genomic sequence, wherein the at least one of the one or more nucleotides is located within about 100 nucleotides of the location in the genomic sequence of the candidate polyadenylation site. In some embodiments, each of the plurality of polyadenylation feature vectors comprises one or more of: (a) a subsequence of the genomic sequence encoded using a 1-of-4 binary vector for a nucleotide selected from adenine (A), thymine (T), cytosine (C), and guanine (G); (b) a subsequence of the genomic sequence encoded using a 1-of-4 binary vector for a nucleotide selected from adenine (A), uracil (U), cytosine (C), and guanine (G); (c) a set of binary components; (d) a set of categorical components; (e) a set of integer components; and (f) a set of real-valued components. In some embodiments, at least one of the set of binary components comprises a value indicative of the presence of a cleavage factor sequence in the candidate polyadenylation site, or a value indicative of the absence of a cleavage factor sequence in the candidate polyadenylation site. In some embodiments, at least one of the set of binary components comprises a value indicative of the presence of a cleavage factor sequence adjacent to the candidate polyadenylation site or a value indicative of the absence of a cleavage factor sequence adjacent to the candidate polyadenylation site. In some embodiments, at least one of the set of real-valued components comprises a log distance, in number of nucleotides in the genomic sequence, from (1) the candidate polyadenylation site to (2) a nearest different candidate polyadenylation site among the plurality of candidate polyadenylation sites. In some embodiments, the at least one of the plurality of polyadenylation feature vectors comprises a feature selected from the group listed in Table 4.

In some embodiments, the method further comprises identifying, for at least one of the plurality of genomic sequences, a maximally preferred candidate polyadenylation site among the plurality of candidate polyadenylation sites, wherein the maximally preferred candidate polyadenylation site has a largest numerical value $r_{max}$ among the set of intermediate representations $r_1, r_2, \ldots, r_n$. In some embodiments, the method further comprises, for at least one of the plurality of genomic sequences, identifying a maximally preferred candidate polyadenylation site among the plurality of candidate polyadenylation sites, wherein the maximally preferred candidate polyadenylation site has a largest numerical value $p_{max}$ among the set of preferences $p_1, p_2, \ldots, p_n$.

In some embodiments, calculating the set of preferences comprises providing a set of numerical parameters, and calculating a multiplication product comprising at least one feature from at least one of the plurality of polyadenylation feature vectors and at least one numerical parameter of the set of numerical parameters. In some embodiments, the method further comprises applying a machine learning algorithm to the plurality of polyadenylation feature vectors to calculate the set of preferences, the machine learning algorithm comprising adjusting at least one numerical parameter of the set of numerical parameters to decrease a loss function. In some embodiments, adjusting the at least one numerical parameter of the set of numerical parameters comprises performing a gradient-based learning procedure. In some embodiments, the gradient-based learning procedure comprises stochastic gradient descent. In some embodiments, the gradient-based learning procedure comprises stochastic gradient descent with momentum and dropout. In some embodiments, the loss function comprises a cross entropy function. In some embodiments, a sum of the set of preferences $p_1, p_2, \ldots, p_n$ equals 1. In some embodiments, each preference $p_i$ among the set of preferences $p_1, p_2, \ldots, p_n$ indicates a probability of selection of an ith candidate polyadenylation site among the plurality of candidate polyadenylation sites. In some embodiments, the first computation module comprises a convolutional neural network, which convolutional neural network is configured to process the plurality of polyadenylation feature vectors to generate the set of intermediate representations $r_1, r_2, \ldots, r_n$ for the plurality of candidate polyadenylation sites. In some embodiments, the intermediate representation for the ith candidate polyadenylation site comprises a numerical value $r_i$, and wherein the second computation module is configured to apply a softmax function to the set of intermediate representations $r_1, r_2, \ldots, r_n$ for the plurality of candidate polyadenylation sites to calculate the set of preferences $p_1, p_2, \ldots, p_n$ for the plurality of candidate polyadenylation sites. In some embodiments, the intermediate representation for the ith candidate polyadenylation site comprises a numerical value $r_i$, and wherein the second computation module is configured to calculate each preference $p_i$ of the set of preferences as $$p_i = \frac{\exp(r_i)}{\exp(r_1) + \exp(r_2) + \ldots + \exp(r_n)},$$

wherein exp is an exponential function or a numerical approximation of an exponential function. In some embodiments, the second computation module is configured to calculate each preference $p_i$ of the set of preferences as $$p_i = \frac{relu(r_i)}{relu(r_1) + relu(r_2) + \ldots + relu(r_n)},$$

wherein relu is a rectified linear function. In some embodiments, the second computation module is configured to calculate each preference $p_i$ of the set of preferences as $$p_i = \frac{m(r_i)}{m(r_1) + m(r_2) + \ldots + m(r_n)},$$

wherein m( ) is a non-negative monotonic function. In some embodiments, a one-to-one correspondence exists between one or more of the plurality of candidate polyadenylation sites of the reference sequence and one or more of the plurality of candidate polyadenylation sites of the variant sequence, and processing the plurality of sets of preferences comprises comparing each of at least one preference in the set of preferences of the reference sequence to the corresponding preference in the set of preferences of the variant sequence which is in one-to-one correspondence. In some embodiments, (c) further comprises calculating a set of changes in preference $\Delta p_1, \Delta p_2, \ldots, \Delta p_n$ corresponding to the plurality of candidate polyadenylation sites of the reference sequence and the plurality of candidate polyadenylation sites of the variant sequence to determine the effect of the antisense oligonucleotide. In some embodiments, the variant sequence obtained by computer processing the reference sequence based on the antisense oligonucleotide, is obtained by replacing one or more nucleotides of the at least the portion of the reference sequence with an N base, a uniform weighting of the 4 bases, or randomly selected bases. In some embodiments, the at least the portion of the reference sequence is within about 100 nucleotides of at least one of the plurality of candidate polyadenylation sites. In some embodiments, the method further comprises applying the trained algorithm to a plurality of polyadenylation feature vectors indicative of a relative positioning of the plurality of candidate polyadenylation sites to calculate the set of preferences.

In some embodiments, the method further comprises administering a therapeutically effective amount of the antisense oligonucleotide to the subject based at least in part on the determined effect of the antisense oligonucleotide. In some embodiments, the determined effect of the antisense oligonucleotide comprises a decreased preference for one or more of the plurality of candidate polyadenylation sites. In some embodiments, the determined effect of the antisense oligonucleotide comprises an increased preference for one or more of the plurality of candidate polyadenylation sites. In some embodiments, the administered therapeutically effective amount of the antisense oligonucleotide modulates polyadenylation of at least one of the plurality of candidate polyadenylation sites in the subject. In some embodiments, the antisense oligonucleotide has a length of about 10 to about 50 nucleotides.

In another aspect, the present disclosure provides a computer system comprising a digital processing device comprising at least one processor, an operating system configured to perform executable instructions, a memory, and a computer program including instructions executable by the digital processing device to create an application for determining an effect of an antisense oligonucleotide on a plurality of candidate polyadenylation sites, the application comprising: a sequence module programmed to provide a plurality of genomic sequences, wherein the plurality of genomic sequences comprises (1) a reference sequence and (2) a variant sequence obtained by computer processing the reference sequence based on the antisense oligonucleotide, wherein the antisense oligonucleotide is complementary to at least a portion of the reference sequence; an identification module programmed to, for each of the plurality of genomic sequences, identify a plurality of candidate polyadenylation sites in the genomic sequence; a feature extraction module programmed to, for each of the plurality of genomic sequences, extract a polyadenylation feature vector for each of the plurality of candidate polyadenylation sites, wherein each of the polyadenylation feature vectors comprises one or more features determined at least based on one or more nucleotides in the genomic sequence; a preference computation module programmed to, for each of the plurality of genomic sequences, apply a trained algorithm to the plurality of polyadenylation feature vectors to calculate a set of preferences $p_1, p_2, \ldots, p_n$ corresponding to the plurality of candidate polyadenylation sites; and a processing module programmed to process the plurality of sets of preferences for each of the plurality of genomic sequences with each other to determine the effect of the antisense oligonucleotide.

In another aspect, the present disclosure provides a non-transitory computer-readable medium comprising machine-executable code that, upon execution by one or more computer processors, implements a method for determining an effect of an antisense oligonucleotide on a plurality of candidate polyadenylation sites, the method comprising: (a) providing a plurality of genomic sequences, wherein the plurality of genomic sequences comprises (1) a reference sequence and (2) a variant sequence obtained by computer processing the reference sequence based on the antisense oligonucleotide, wherein the antisense oligonucleotide is complementary to at least a portion of the reference sequence; and (b) for each of the plurality of genomic sequences: identifying a plurality of candidate polyadenylation sites in the genomic sequence; extracting a polyadenylation feature vector for each of the plurality of candidate polyadenylation sites, wherein each of the polyadenylation feature vectors comprises one or more features determined at least based on one or more nucleotides in the genomic sequence; and applying a trained algorithm to the plurality of polyadenylation feature vectors to calculate a set of preferences $p_1, p_2, \ldots, p_n$ corresponding to the plurality of candidate polyadenylation sites; and (c) processing the plurality of sets of preferences for each of the plurality of genomic sequences with each other to determine the effect of the antisense oligonucleotide.

In another aspect, the present disclosure provides a system for determining an effect of an antisense oligonucleotide on a plurality of candidate polyadenylation sites, the system comprising: a database comprising a plurality of genomic sequences generated from deoxyribonucleic acid (DNA) or ribonucleic acid (RNA) molecules, wherein the plurality of genomic sequences comprises (1) a reference sequence and (2) a variant sequence obtained by computer processing the reference sequence based on the antisense oligonucleotide, wherein the antisense oligonucleotide is complementary to at least a portion of the reference sequence; and one or more computer processors operatively coupled to the database, wherein the one or more computer processors are individually or collectively programmed to: (a) for each of the plurality of genomic sequences, identify a plurality of candidate polyadenylation sites in the genomic sequence; (b) for each of the plurality of genomic sequences, extract a polyadenylation feature vector for each of the plurality of candidate polyadenylation sites, wherein each of the polyadenylation feature vectors comprises one or more features determined at least based on one or more nucleotides in the genomic sequence; (c) for each of the plurality of genomic sequences, apply a trained algorithm to the plurality of polyadenylation feature vectors to calculate a set of preferences $p_1, p_2, \ldots, p_n$ for the plurality of candidate polyadenylation sites; and (d) process the plurality of sets of preferences for each of the plurality of genomic sequences with each other to determine the effect of the antisense oligonucleotide.

In another aspect, the present disclosure provides a method for identifying tissue-specific polyadenylation features, the method comprising: (a) providing a set of genomic sequences; (b) for each of the set of genomic sequences: identifying a plurality of candidate polyadenylation sites in the genomic sequence; extracting a polyadenylation feature vector for each of the plurality of candidate polyadenylation sites, wherein each of the polyadenylation feature vectors comprises one or more features determined at least based on one or more nucleotides in the genomic sequence; and applying a trained algorithm to the plurality of polyadenylation feature vectors to calculate a set of preferences $p_1, p_2, \ldots, p_n$ for the plurality of candidate polyadenylation sites; and (c) computer processing the set of preferences for each of the set of genomic sequences to identify the tissue-specific polyadenylation features.

In some embodiments, calculating the set of preferences for each of the set of genomic sequences comprises, for each of the plurality of candidate polyadenylation sites, computer processing a first computation module the plurality of polyadenylation feature vectors of the genomic sequence to calculate an intermediate representation $r_i$ for an ith candidate polyadenylation site, the intermediate representation comprising at least one numerical value; and computer processing by a second computation module the set of intermediate representations $r_1, r_2, \ldots, r_n$ for the plurality of candidate polyadenylation sites to calculate the set of preferences $p_1, p_2, \ldots, p_n$ corresponding to the plurality of candidate polyadenylation sites. In some embodiments, the reference sequence is (i) derived from a human genome, (ii) obtained by sequencing deoxyribonucleic acid (DNA) or ribonucleic acid (RNA) of a bodily sample obtained from a subject, or (iii) a genetic aberration thereof. In some embodiments, the genetic aberration comprises a single nucleotide variant (SNV) or an insertion or deletion (indel). In some embodiments, at least one of the plurality of polyadenylation feature vectors comprises a feature determined at least based on one or more nucleotides in the genomic sequence, wherein the at least one of the one or more nucleotides is located within about 100 nucleotides of the location in the genomic sequence of the candidate polyadenylation site. In some embodiments, each of the plurality of polyadenylation feature vectors comprises one or more of: (a) a subsequence of the genomic sequence encoded using a 1-of-4 binary vector for a nucleotide selected from adenine (A), thymine (T), cytosine (C), and guanine (G); (b) a subsequence of the genomic sequence encoded using a 1-of-4 binary vector for a nucleotide selected from adenine (A), uracil (U), cytosine (C), and guanine (G); (c) a set of binary components; (d) a set of categorical components; (e) a set of integer components; and (f) a set of real-valued components. In some embodiments, at least one of the set of binary components comprises a value indicative of the presence of a cleavage factor sequence in the candidate polyadenylation site, or a value indicative of the absence of a cleavage factor sequence in the candidate polyadenylation site. In some embodiments, at least one of the set of binary components comprises a value indicative of the presence of a cleavage factor sequence adjacent to the candidate polyadenylation site or a value indicative of the absence of a cleavage factor sequence adjacent to the candidate polyadenylation site. In some embodiments, at least one of the set of real-valued components comprises a log distance, in number of nucleotides in the genomic sequence, from (1) the candidate polyadenylation site to (2) a nearest different candidate polyadenylation site among the plurality of candidate polyadenylation sites. In some embodiments, the at least one of the plurality of polyadenylation feature vectors comprises a feature selected from the group listed in Table 4.

In some embodiments, the method further comprises identifying, for at least one of the plurality of genomic sequences, a maximally preferred candidate polyadenylation site among the plurality of candidate polyadenylation sites, wherein the maximally preferred candidate polyadenylation site has a largest numerical value $r_{max}$ among the set of intermediate representations $r_1, r_2, \ldots, r_n$. In some embodiments, the method further comprises, for at least one of the plurality of genomic sequences, identifying a maximally preferred candidate polyadenylation site among the plurality of candidate polyadenylation sites, wherein the maximally preferred candidate polyadenylation site has a largest numerical value $p_{max}$ among the set of preferences $p_1, p_2, \ldots, p_n$. In some embodiments, calculating the set of preferences comprises providing a set of numerical parameters, and calculating a multiplication product comprising at least one feature from at least one of the plurality of polyadenylation feature vectors and at least one numerical parameter of the set of numerical parameters. In some embodiments, the method further comprises applying a machine learning algorithm to the plurality of polyadenylation feature vectors to calculate the set of preferences, the machine learning algorithm comprising adjusting at least one numerical parameter of the set of numerical parameters to decrease a loss function. In some embodiments, adjusting the at least one numerical parameter of the set of numerical parameters comprises performing a gradient-based learning procedure. In some embodiments, the gradient-based learning procedure comprises stochastic gradient descent. In some embodiments, the gradient-based learning procedure comprises stochastic gradient descent with momentum and dropout. In some embodiments, the loss function comprises a cross entropy function. In some embodiments, a sum of the set of preferences $p_1, p_2, \ldots, p_n$ equals 1. In some embodiments, each preference $p_i$ among the set of preferences $p_1, p_2, \ldots, p_n$ indicates a probability of selection of an ith candidate polyadenylation site among the plurality of candidate polyadenylation sites. In some embodiments, the first computation module comprises a convolutional neural network, which convolutional neural network is configured to process the plurality of polyadenylation feature vectors to generate the set of intermediate representations $r_1, r_2, \ldots, r_n$ for the plurality of candidate polyadenylation sites. In some embodiments, the intermediate representation for the ith candidate polyadenylation site comprises a numerical value $r_i$, and wherein the second computation module is configured to apply a softmax function to the set of intermediate representations $r_1, r_2, \ldots, r_n$ for the plurality of candidate polyadenylation sites to calculate the set of preferences $p_1, p_2, \ldots, p_n$ for the plurality of candidate polyadenylation sites. In some embodiments, the intermediate representation for the ith candidate polyadenylation site comprises a numerical value $r_i$, and wherein the second computation module is configured to calculate each preference of the set of preferences $p_i$ as $$p_i = \frac{\exp(r_i)}{\exp(r_1) + \exp(r_2) + \ldots + \exp(r_n)},$$

wherein exp is an exponential function or a numerical approximation of an exponential function. In some embodiments, the second computation module is configured to calculate each preference $p_i$ of the set of preferences as $$p_i = \frac{relu(r_i)}{relu(r_1) + relu(r_2) + \ldots + relu(r_n)},$$

wherein relu is a rectified linear function. In some embodiments, the second computation module is configured to calculate each preference $p_i$ of the set of preferences as $$p_i = \frac{m(r_i)}{m(r_1) + m(r_2) + \ldots + m(r_n)},$$

wherein m( ) is a non-negative monotonic function. In some embodiments, the method further comprises applying the trained algorithm to a plurality of polyadenylation feature vectors indicative of a relative positioning of the plurality of candidate polyadenylation sites to calculate the set of preferences. In some embodiments, (c) further comprises, for each of the set of genomic sequences, for each of the plurality of candidate polyadenylation sites, computing a gradient of the set of preferences generated by the convolutional neural network with respect to the features of the polyadenylation feature vector of the candidate polyadenylation site, thereby generating a plurality of feature saliency values of the features of the polyadenylation feature vector of the candidate polyadenylation site. In some embodiments, the method further comprises, for each of the set of genomic sequences, for each of the plurality of candidate polyadenylation sites, sorting the features of the polyadenylation feature vector of the candidate polyadenylation site based at least in part on the feature saliency values of the features of the polyadenylation feature vector. In some embodiments, the method further comprises, for each of the set of genomic sequences, for each of the plurality of candidate polyadenylation sites, classifying the features of the polyadenylation feature vector of the candidate polyadenylation site as increasing or decreasing a strength of a polyadenylation site, based at least in part on the feature saliency values of the features of the polyadenylation feature vector of the candidate polyadenylation site. In some embodiments, (c) further comprises, for each of the set of genomic sequences, for each of the plurality of candidate polyadenylation sites, identifying a feature of the polyadenylation feature vector of the candidate polyadenylation site as a tissue-specific polyadenylation feature based at least in part on whether the feature has a feature saliency value that meets a predetermined criterion. In some embodiments, the plurality of candidate polyadenylation sites comprises a plurality of tissue-specific polyadenylation sites and a plurality of constitutive polyadenylation sites. In some embodiments, the predetermined criterion is a feature saliency value having a statistically greater effect on tissue-specific polyadenylation sites compared to constitutive polyadenylation sites, that meets a predetermined threshold. In some embodiments, the predetermined threshold is that the feature saliency value has a statistically greater effect on the plurality of tissue-specific polyadenylation sites compared to the plurality of constitutive polyadenylation sites, with a P-value of at most a P-value threshold equal to 0.05 divided by a number of features of the polyadenylation feature vector of the candidate polyadenylation site. In some embodiments, the predetermined threshold is that the feature saliency value has a statistically greater effect on the plurality of tissue-specific polyadenylation sites compared to the plurality of constitutive polyadenylation sites, with a P-value of at most a P-value threshold equal to 0.03 divided by a number of features of the polyadenylation feature vector of the candidate polyadenylation site. In some embodiments, the predetermined threshold is that the feature saliency value has a statistically greater effect on the plurality of tissue-specific polyadenylation sites compared to the plurality of constitutive polyadenylation sites, with a P-value of at most a P-value threshold equal to 0.01 divided by a number of features of the polyadenylation feature vector of the candidate polyadenylation site. In some embodiments, the method further comprises, for each of the set of genomic sequences, for each of the plurality of candidate polyadenylation sites, classifying the features of the polyadenylation feature vector of the candidate polyadenylation site as increasing or decreasing a likelihood of a polyadenylation site to be tissue-specific, based at least in part on the feature saliency values of the features of the polyadenylation feature vector of the candidate polyadenylation site. In some embodiments, the method further comprises processing the plurality of feature saliency values to generate a feature saliency map. In some embodiments, the method further comprises identifying one or more genomic regions for polyadenylation-targeted therapeutic purposes based at least in part on the feature saliency map. In some embodiments, the one or more genomic regions for polyadenylation-targeted therapeutic purposes comprise one or more of: an oligonucleotide targeted Type 1 Poly(A) signal, a location of a Type 4 Poly(A) signal, and an oligonucleotide Type 2 Poly(A) signal.

In another aspect, the present disclosure provides a computer system comprising a digital processing device comprising at least one processor, an operating system configured to perform executable instructions, a memory, and a computer program including instructions executable by the digital processing device to create an application for identifying tissue-specific polyadenylation features, the application comprising: a sequence module programmed to provide a set of genomic sequences; an identification module programmed to, for each of the set of genomic sequences, identify a plurality of candidate polyadenylation sites in the genomic sequence; a feature extraction module programmed to, for each of the set of genomic sequences, extract a polyadenylation feature vector for each of the plurality of candidate polyadenylation sites, wherein each of the polyadenylation feature vectors comprises one or more features determined at least based on one or more nucleotides in the genomic sequence; a preference computation module programmed to, for each of the plurality of genomic sequences, apply a trained algorithm to the plurality of polyadenylation feature vectors to calculate a set of preferences $p_1, p_2, \ldots, p_n$ for the plurality of candidate polyadenylation sites; and a processing module programmed to process the set of preferences for each of the set of genomic sequences to identify the tissue-specific polyadenylation features.

In another aspect, the present disclosure provides a non-transitory computer-readable medium comprising machine-executable code that, upon execution by one or more computer processors, implements a method for identifying tissue-specific polyadenylation features, the method comprising: (a) providing a set of genomic sequences; (b) for each of the set of genomic sequences: identifying a plurality of candidate polyadenylation sites in the genomic sequence; extracting a polyadenylation feature vector for each of the plurality of candidate polyadenylation sites, wherein each of the polyadenylation feature vectors comprises one or more features determined at least based on one or more nucleotides in the genomic sequence; and applying a trained algorithm to the plurality of polyadenylation feature vectors to calculate a set of preferences $p_1, p_2, \ldots, p_n$ for the plurality of candidate polyadenylation sites; and (c) processing the set of preferences for each of the set of genomic sequences to identify the tissue-specific polyadenylation features.

In another aspect, the present disclosure provides a system for identifying tissue-specific polyadenylation features, the system comprising: a database comprising a set of genomic sequences generated from deoxyribonucleic acid (DNA) or ribonucleic acid (RNA) molecules; and one or more computer processors operatively coupled to the database, wherein the one or more computer processors are individually or collectively programmed to: (a) for each of the set of genomic sequences, identify a plurality of candidate polyadenylation sites in the genomic sequence; (b) for each of the set of genomic sequences, extract a polyadenylation feature vector for each of the plurality of candidate polyadenylation sites, wherein each of the polyadenylation feature vectors comprises one or more features determined at least based on one or more nucleotides in the genomic sequence; (c) for each of the set of genomic sequences, apply a trained algorithm to the plurality of polyadenylation feature vectors to calculate a set of preferences $p_1, p_2, \ldots, p_n$ for the plurality of candidate polyadenylation sites; and (d) process the set of preferences for each of the set of genomic sequences to identify the tissue-specific polyadenylation features.

In another aspect, the present disclosure provides a method for determining an effect of an antisense oligonucleotide on a plurality of candidate polyadenylation sites, comprising processing a sequence of the antisense oligonucleotide to obtain a change in preference corresponding to each of the plurality of candidate polyadenylation sites, to identify at least one of the plurality of candidate polyadenylation sites as having a change in preference that meets a threshold.

In some embodiments, processing the sequence of the antisense oligonucleotide comprises: (i) providing (1) a reference sequence and (2) a variant sequence obtained by computer processing the reference sequence based on the antisense oligonucleotide, wherein the antisense oligonucleotide is complementary to at least a portion of the reference sequence; (ii) using a trained algorithm to calculate (1) a first set of preferences for a plurality of candidate polyadenylation sites of the reference sequence and (2) a second set of preferences for a plurality of candidate polyadenylation sites of the variant sequence; and (iii) computer processing the first set of preferences with the second set of preferences to obtain the plurality of changes in preference. In some embodiments, (iii) further comprises calculating a set of changes in preference $\Delta p_1, \Delta p_2, \ldots, \Delta p_n$ corresponding to the plurality of candidate polyadenylation sites of the reference sequence and the plurality of candidate polyadenylation sites of the variant sequence. In some embodiments, the variant sequence obtained by computer processing the reference sequence based on the antisense oligonucleotide, is obtained by replacing one or more nucleotides of the at least the portion of the reference sequence with an N base, a uniform weighting of the 4 bases, or randomly selected bases. In some embodiments, the reference sequence is (i) derived from a human genome, (ii) obtained by sequencing deoxyribonucleic acid (DNA) or ribonucleic acid (RNA) of a bodily sample obtained from a subject, or (iii) a genetic aberration thereof. In some embodiments, the method further comprises administering a therapeutically effective amount of the antisense oligonucleotide to the subject based at least in part on the identified at least one of the plurality of candidate polyadenylation sites. In some embodiments, the trained algorithm comprises a machine learning algorithm. In some embodiments, each preference $p_i$ among the set of preferences $p_1, p_2, \ldots, p_n$ indicates a probability of selection of an ith candidate polyadenylation site among the plurality of candidate polyadenylation sites. In some embodiments, the antisense oligonucleotide has a length of about 10 to about 50 nucleotides. In some embodiments, the method further comprises determining a tissue-specific effect of the antisense oligonucleotide based at least in part on whether a plurality of polyadenylation feature vectors of the plurality of candidate polyadenylation sites comprises tissue-specific polyadenylation features. In some embodiments, the method further comprises determining the tissue-specific effect of the antisense oligonucleotide with a P-value of at most about 0.05. In some embodiments, the method further comprises determining the tissue-specific effect of the antisense oligonucleotide with a P-value of at most about 0.03. In some embodiments, the method further comprises determining the tissue-specific effect of the antisense oligonucleotide with a P-value of at most about 0.01. In some embodiments, the method further comprises determining the tissue-specific effect of the antisense oligonucleotide based at least in part on whether the plurality of polyadenylation feature vectors of the plurality of candidate polyadenylation sites comprises one or more tissue-specific polyadenylation features selected from the group listed in Table 5.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

DETAILED DESCRIPTION

Figure 1:
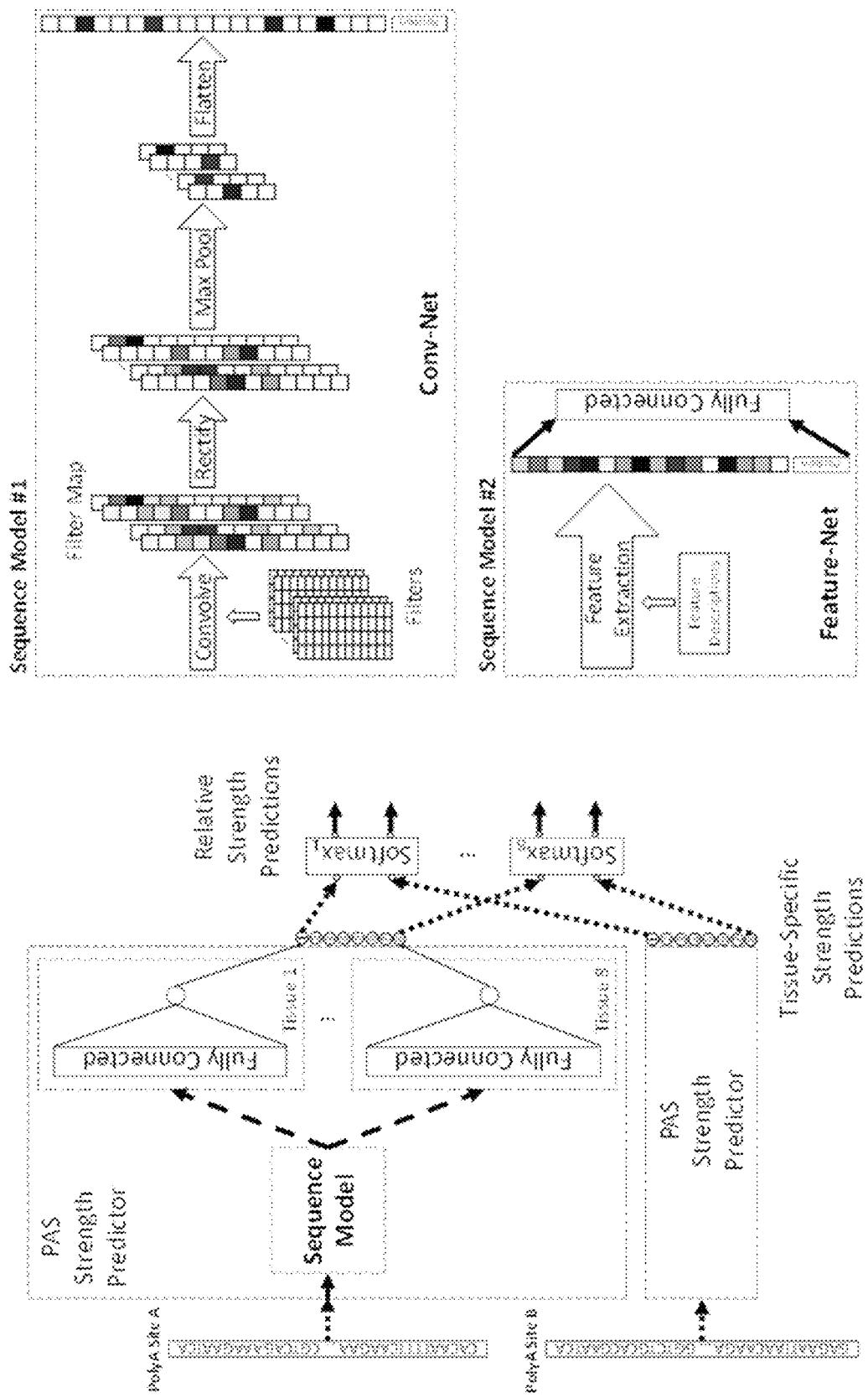
FIG. 1 illustrates a schematic of the components of the neural network that represent the polyadenylation model (left) and a comparison of two architectures for the sequence model, a convolutional neural network that operates directly on sequences and a fully-connected neural network that takes in a feature vector processed by a feature extraction pipeline (right). Figure discloses the "PolyA Site B" sequences as SEQ ID NOS 2-3 and the "PolyA Site A" sequences as SEQ ID NOS 4-5, all respectively, in order of appearance.
Figure 2:
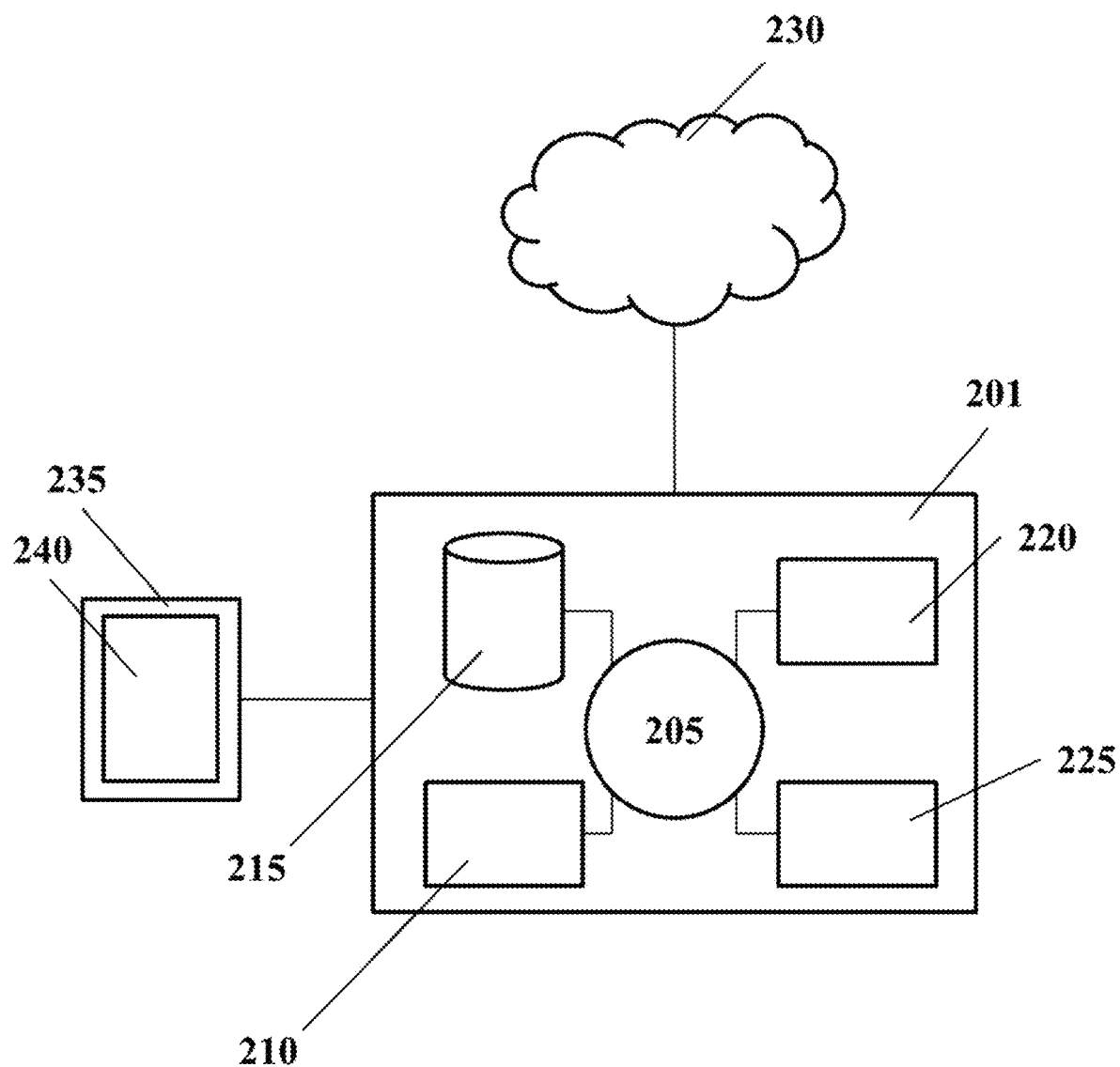
FIG. 2 shows a computer system that is programmed or otherwise configured to implement methods provided herein.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The term "polyadenylation site," as used herein, generally refers to a site in a genome that may be involved in a polyadenylation procedure (e.g., cleavage of a precursor messenger ribonucleic acid (RNA), followed by the addition of a poly(A) tail to form a mature messenger RNA (mRNA)). A single precursor messenger RNA (pre-mRNA) may have a corresponding set of one or more polyadenylation sites, each of which is capable of being subjected to cleavage and polyadenylation.

The term "sample," as used herein, generally refers to a biological sample. A sample may be a fluid or tissue sample. The sample nucleic acid molecules may be deoxyribonucleic acid (DNA) molecules, RNA molecules, or both. The sample may be a tissue sample. The sample may be plasma, serum or blood (e.g., whole blood sample). The sample may be a cell-free sample (e.g., cell-free DNA, cfDNA). A bodily sample may be derived from any organ, tissue or biological fluid. A bodily sample can comprise, for example, a bodily fluid or a solid tissue sample. An example of a solid tissue sample is a tumor sample, e.g., from a solid tumor biopsy. Bodily fluids may include, for example, blood, serum, plasma, tumor cells, saliva, urine, lymphatic fluid, prostatic fluid, seminal fluid, milk, sputum, stool, tears, and derivatives of these.

The term "sequencing read," as used herein, generally refers to a sequence generated by a nucleic acid sequencer. The sequence may be in digital form, such as a digital sequence stored in computer memory. The nucleic acid sequencer may be a massively parallel array sequencer (e.g., Illumina, Ion Torrent, Pacific Biosciences of California, etc.) or single molecule sequencer (e.g., Oxford Nanopore). The nucleic acid sequencer may be a high throughput sequencer.

Polyadenylation is a mechanism that may occur within human cells. In a polyadenylation process, a poly(A) tail may be added to a messenger RNA (mRNA). The detection of polyadenylation sites depends on patterns within an mRNA sequence and corresponding patterns within a DNA sequence. Genetic variation in a nucleic acid (e.g., mutations in a DNA sequence or an mRNA sequence) can disrupt these patterns. If one or more nucleotides are mutated in a nucleic acid (e.g., an mRNA strand or a DNA strand), the effect of this genetic variation may cause polyadenylation to occur at a different polyadenylation site. This effect may result in functional consequences, such as one or more phenotype changes leading to a disease or acting as contributing factors in a disease.

Understanding how genetic variation may influence the selection of polyadenylation sites may be important for understanding diseases such as cancers and neurological disorders, as well as other gross phenotypes, such as potentially for aging, developing therapies that act on RNA or DNA, and developing companion diagnostics that indicate under which genetic circumstances a therapy may be effective.

Polyadenylation may be a mechanism responsible for regulating mRNA function, stability, localization, and translation efficiency. As much as 70% of human genes may be subject to alternative polyadenylation (APA), and widespread mechanisms may influence its regulation. By selecting which polyadenylation site (PAS) among a plurality of possible polyadenylation sites is cleaved, different transcript isoforms that vary either in their coding sequences or in their 3' untranslated region (3'-UTR) can be produced. Transcripts differentially cleaved can influence how they are regulated. For example, longer variants can harbor additional destabilization elements that alter a transcript's stability, and shortened variants can escape regulation from microRNAs, which have been observed in various cancers. Furthermore, APA can be tissue-dependent, so a single gene can generate different transcripts, for instance, based on the tissue in which it is expressed. One mechanism of APA regulation may occur at the level of the sequences of the transcript. The presence or absence of certain regulatory elements can influence which PAS is selected. PAS selection may also be influenced by a site's position relative to other sites. A computational model that can accurately predict how polyadenylation is affected by genomic features as well as cellular context may be highly desirable to understand this widespread phenomenon. Moreover, several inherited diseases have been linked to errors in 3'-end processing. Such a model may enable the exploration of the effects of genetic variations on polyadenylation and their implications for disease.

The present disclosure provides systems and methods for determining effects of genetic variants on selection of polyadenylation sites during polyadenylation processes. In an aspect, the present disclosure provides a polyadenylation code, a computational model that can predict alternative polyadenylation patterns from transcript sequences. Many existing approaches of classifying whether a stretch of sequence contains a PAS, or characterizing whether a PAS is tissue-specific, may be aimed at improving gene annotations and understanding which features are involved in APA regulation, and may not address the question of predicting how APA sites are variably selected. This question is addressed by developing a model that can predict a PAS strength score that describes or corresponds to the efficiency in which a PAS is recognized by 3'-end processing machinery for cleavage and polyadenylation. The ability to predict PAS strength may enable this model to generalize to multiple prediction tasks, even though it may not be explicitly trained for them. For example, the model can be applied to a gene with multiple PAS to determine the relative transcript isoforms that may be produced in a tissue-specific manner. The model can predict the consequence of nucleotide substitutions on PAS strength, which can be used to prioritize genetic variants that affect polyadenylation. It can be used to assess the effects of anti-sense oligonucleotides to alter transcript abundance. It can also scan the 3'-UTR of the human genome to find potential PAS. The present disclosure provides examples of these applications and methods to analyze on how different features affect the predictions of the model.

Inferring the Strength of a Polyadenylation Site

Using systems and methods of the present disclosure, a score can be calculated that describes or corresponds to the strength of a PAS, or the efficiency in which it is recognized by the 3'-end processing machinery. Such a task may be straightforward if this target variable is directly measurable. However, current sequencing protocols may provide only a measurement of the relative transcript abundance from APA. Some approaches to quantify the strength of a PAS may, for example, use normalized read counts, but quantification can be affected by factors such as sequencing biases, transcript length, and RNA decay. Some approaches may classify PAS strength based on whether a canonical polyadenylation signal or other reported sequence elements are present near the PAS. The present disclosure provides systems and methods to predict a quantitative description of the strength of a PAS by modeling it as a hidden variable, and to infer it from data. Moreover, the position of a PAS relative to neighboring sites can affect its selection. Some biological processes and tissues may favor PAS at the distal end, whereas cells under disease states may tend to utilize PAS that are more proximal. To account for this, the model may include a variable that accounts for the distance between neighboring sites during training. Even though the position of a PAS is modeled, a desirable characteristic of the predictor may be that during inference, positional information may be optional. This can be useful in regions of the genome where there are insufficient annotation sources to ascertain the distance to a nearby PAS. This may also enable this model to be applied to any DNA sequence associated with a site, optionally for the bases within to be modified, and the predicted effect on polyadenylation regulation to be observed. To determine which PAS in a gene with multiple sites is more likely to be selected, the model can be applied to each PAS separately to compare their relative strengths. Optionally, their positions can be factored in to the model's prediction if annotation sources are available in order to get a better estimate.

Polyadenylation Code Models

Using systems and methods of the present disclosure, a polyadenylation code model may be constructed and analyzed. The polyadenylation code may refer to a model that can infer tissue-specific PAS strength scores from sequence, and optionally account for the influence of position if it is provided. The model may take as input a sequence of length 200 bases centered on a PAS. Two or more models which operate on the sequence differently may be benchmarked.

A first model may be built on hand-crafted features. Features may be extracted or derived from genomic sequences (e.g., higher level engineered features, based on composition or counts of multiple bases). Alternatively, features may simply comprise at least a portion of the sequence itself (e.g., lower level raw sequences, such as one-hot encoding of individual bases). The genomic sequence may be processed by a feature extraction pipeline, which divides the sequence into 4 regions relative to the PAS (as described, for example, in Example 8, and as described, for example, by Hu et al., Bioinformatic identification of candidate cis-regulatory elements involved in human mRNA polyadenylation, RNA, 2005; which is hereby incorporated by reference in its entirety). Some feature may be limited to specific regions, namely the polyadenylation signals in the 5'-5' and 5'-3' regions, and hexamers defined by Hu et al. Other features may be computed in all regions, including counts of RNA-binding protein (RBP) motifs that may be involved in polyadenylation, all possible 1 to 4 n-mers counts, and nucleosome positioning features (as described, for example, by van der Heijden et al., Sequence-based prediction of single nucleosome positioning and genome-wide nucleosome occupancy, Proc. Natl. Acad. Sci. U.S.A, 2012; which is hereby incorporated by reference in its entirety). The feature vector may be mapped to a fully-connected neural network. Such a model may be referred to as a Feature-Net.

A second model may directly learn from the genomic sequence, using a convolutional neural network (Conv-Net) architecture, which can efficiently discover sequence patterns without prior knowledge even when the location of the patterns is unknown. The Conv-Net may comprise tunable motif filters which are free to adapt to the input sequence to optimize the predictive performance of the model. It may also contain pooling operations that enable the model to focus on select locations in the input sequence whose composition may maximally activate the motif filters.

To account for the positional preference of PAS, the log distance between sites may also be an input feature for both models. Given two sites, the proximal (5') site may have a position feature of 0, whereas the distal (3') site may have a position feature that is equal to the logarithm of the distance between the distal site and the proximal site.

FIG. 1 shows a schematic of both the first model and the second model. First, the sequences are transformed by the Feature-Net and Conv-Net into a hidden representation. The Feature-Net may perform feature extraction on the sequence to generate a feature vector, which may then be mapped to a fully-connected neural network. The Conv-Net may apply filters to convolve the sequence into a filter map, which may then be rectified, pooled, and flattened. Next, the hidden representation may be processed by separate fully-connected hidden layers of a PAS strength predictor to make tissue-specific predictions. The architecture therefore factors predictions into two components: a score that describes or corresponds to the tissue-specific PAS strength, followed by predictions that represent the relative abundance of transcripts from RNA-Seq experiments between two competing PAS. The parameters of the fully-connected layers model the cell state of tissues, which describes or corresponds to the steady-state environment of the cell, such as the protein concentrations in the cytosol, that can affect transcriptional modifications. These cell state parameters may not be explicitly defined in terms of what they consist of or how they factor in the predictions, but rather may be simply modeled as hidden variables and be learned from data. For example, a similar approach can be used in a splicing regulatory model (as described, for example, by Xiong et al., The human splicing code reveals new insights into the genetic determinants of disease, Science, 2014; which is hereby incorporated by reference in its entirety).

Seven distinct tissue types may be available in the dataset used to train the models. Since there may be two sets of sequencing reads for the naïve B-cells obtained from different donors (as described, for example, by Lianoglou et al., Ubiquitously transcribed genes use alternative polyadenylation to achieve tissue-specific expression, Genes Dev., 2013; which is hereby incorporated by reference in its entirety), they can be treated as separate tissues, and so the model described herein have eight polyadenylation strength prediction outputs. A choice may be made to not rely on evolutionary conservation to force the models to learn patterns from the genome itself (as described, for example, by Leung et al., Machine Learning in Genomic Medicine: A Review of Computational Problems and Data Sets, Proc. IEEE, 2016; which is hereby incorporated by reference in its entirety). In addition, additional data sources such as conservation tracks or expression data may not be used as input. For the model to be widely applicable to multiple tasks, it may be beneficial for the input to be easily obtainable, such as sequences. Requiring any inputs beyond sequences may make a model more difficult to apply across diverse problem domains.

A training example may comprise two PAS from the same gene and may require the model to predict their relative strengths, which can be interpreted as the probability that each site may be selected for cleavage and polyadenylation. The relative strength may be measured by the read counts from RNA-Seq that have been mapped to each site. As shown in FIG. 1, a softmax function may be used to squash the real-valued predictions (e.g., tissue-specific strength predictions) from the PAS strength predictor into a normalized score that can be interpreted as the probability that one PAS is chosen over the other (e.g., relative strength predictions). The predictions are penalized against training targets of the relative abundances of transcripts for these PAS, which is measured from the sequencing experiment. Results described herein may be based on the predictions from the PAS strength predictor (e.g., the logits) instead of the relative strength predictions that follows the softmax.

The predictive model may be applied to multiple tasks, even though it may be trained only to the task of modeling competing site selection. Predictions for these other tasks may be evaluated without any additional task-specific training or data augmentation to demonstrate the general applicability of this model.

Assembling a Polyadenylation Atlas

Analysis of human polyadenylation events may be confined to the 3'-UTR, where PAS are most frequently located. Using systems and methods of the present disclosure, a polyadenylation atlas may be assembled. To identify the 3'-UTR regions of the human genome, 3'-UTR annotations, such as those from UCSC (as described, for example, by Kent et al., The human genome browser at UCSC, Genome Res., 2002; which is hereby incorporated by reference in its entirety), GENCODE (as described, for example, by Harrow et al., GENCODE: the reference human genome annotation for the ENCODE project, Genome Res., 2012; which is hereby incorporated by reference in its entirety), RefSeq (as described, for example, by Pruitt et al., NCBI Reference Sequence (RefSeq): a curated non-redundant sequence database of genomes, transcripts and proteins, *Nucleic Acids Res.*, 2005; which is hereby incorporated by reference in its entirety), and Ensembl (as described, for example, by Yates et al., Ensembl 2016, *Nucleic Acids Res.*, 2016; which is hereby incorporated by reference in its entirety), may be combined, where overlapping regions are merged, and each 3'-UTR segment may be further extended by about 500 bases to capture potential uncharacterized regions.

Then, to generate a comprehensive atlas of PAS, multiple polyadenylation annotations and reads from different 3'-end sequencing experiments may be mapped to the 3'-UTR to generate an atlas of human PAS. The polyadenylation annotations used may include PolyA_DB 2 (as described, for example, by Lee et al., PolyA_DB 2: mRNA polyadenylation sites in vertebrate genes, *Nucleic Acids Res.*, 2007; which is hereby incorporated by reference in its entirety), GENCODE, and APADB (as described, for example, by Müller et al., APADB: a database for alternative polyadenylation and microRNA regulation events, *Database (Oxford)*, 2014; which is hereby incorporated by reference in its entirety).

Mapped reads that lie in the 3'-UTR from PolyA-Seq (as described, for example, by Derti et al., A quantitative atlas of polyadenylation in five mammals, *Genome Res.*, 2012; which is hereby incorporated by reference in its entirety) and 3'-Seq (as described, for example, by Lianoglou et al., Ubiquitously transcribed genes use alternative polyadenylation to achieve tissue-specific expression, *Genes Dev.*, 2013; which is hereby incorporated by reference in its entirety) may also be used to expand the repertoire of PAS, where the genomic positions of reads from these sequencing experiments are used to mark the locations of PAS in the genome. PAS from different sources may largely overlap, but some sites can be unique to one study due to the differences in cell lines or tissue types as well as sequencing protocol. Due to the inexact nature of 3'-end processing, PAS that are within 50 bases of each other may be clustered, and the resulting peak may be marked as the location of the PAS. The final PAS atlas may contain about 19,320 3'-UTR regions with two or more PAS from genes in the hg19 assembly for a total of 92,218 sites.

Quantifying Relative Polyadenylation Site Usage

The model may be trained from the relative abundance of transcripts from a 3'-end sequencing experiment of seven distinct human tissues, including the brain, breast, embryonic stem (ES) cells, ovary, skeletal muscle, testis, and two samples of naïve B cells (as described, for example, by Lianoglou et al., Ubiquitously transcribed genes use alternative polyadenylation to achieve tissue-specific expression, *Genes Dev.*, 2013; which is hereby incorporated by reference in its entirety). Other cell lines may also be available in the dataset, but may not be used. The version of aligned reads which have been processed through the studies' computational pipeline may be used, which include removal of internally primed and antisense reads, as well as application of minimum expression requirements to reduce sequencing noise. These reads may be assigned to the PAS atlas, resulting in read counts associated with each PAS.

To quantify the relative PAS usage for each gene which acts as the target to train the model, a Beta model derived from Bayesian inference (as described, for example, by Xiong et al., Probabilistic estimation of short sequence expression using RNA-Seq data and the positional bootstrap, 2016; which is hereby incorporated by reference in its entirety) may be adopted, treating the percent read counts of one site relative to another site as the parameter of a Bernoulli distribution. With this model, the relative PAS usage of one site relative to another, referred to as $\Phi$, can be given by $p(\Phi)=\text{Beta}(1+N_{site1}, 1+N_{site2})$, where $N_{site1}$ and $N_{site2}$ are the number of reads from two different sites. The mean of this distribution can be used as the target to train the model, that is, the PAS usage of site 1 relative to site 2 is $(1+N_{site1})/(2+N_{site1}+N_{site2})$. For 3'-UTR regions with more than 2 PAS, different combinations of pairs of sites may be generated as training targets and quantified as above. An assumption may be that the relative strength of neighboring PAS can be described by the relative read counts at those sites, even if there are other sites present in the same gene. This assumption may simplify the architecture of the computational model and quantification of relative strength between sites.

Training Neural Networks

The model may be constructed and trained in Python using the TensorFlow library (as described, for example, by Abadi et al., TensorFlow: Large-Scale Machine Learning on Heterogeneous Distributed Systems, 2015; and by Rampasek et al., TensorFlow: Biology's Gateway to Deep Learning?, *Cell Syst.*, 2016; each of which is hereby incorporated by reference in its entirety). Hidden units of the neural network may comprise rectified linear activation units. For the Feature-Net, the feature vectors may be normalized with mean zero and standard deviation of one. For the Conv-Net, the input may use a one-hot encoding representation for each of the 4 nucleotides. For a sequence of length n, the dimension of the input may be 4×n. Padding may be inserted at both ends of the input so that the motif filters can be applied to each position of the sequence from beginning to end. For a motif filter of length m, the additional padding on each side of the sequence may be 4×(m−1), where these additional padding may be filled with the value 0.25, equivalent to an N nucleotide in IUPAC notation. This approach may be similar to that described by Alipanahi et al. (Predicting the sequence specificities of DNA- and RNA-binding proteins by deep learning, *Nat. Biotechnol.*, 2015; which is hereby incorporated by reference in its entirety).

Each training example may consist of a pair of PAS from a gene, where the input is the two sites' genomic sequences, and the target is their relative read counts computed as described elsewhere herein. For genes with more than 2 PAS, different combinations of pairs of sites may be generated as examples. Only examples with more than 10 reads may be kept. This may result in a dataset of 64,572 examples, which is split for training and testing.

The parameters of the neural network may be initialized (as described, for example, by Glorot et al., Understanding the difficulty of training deep feedforward neural networks, *Proc. 13th Int. Conf Artif Intell. Stat.*, 2010; which is hereby incorporated by reference in its entirety). Next, the parameters of the neural network may be trained using a stochastic gradient descent method with momentum and dropout (as described, for example, by Hinton et al., Improving neural networks by preventing co-adaptation of feature detectors, *arXiv Prepr. arXiv*1207.0580, 2012; which is hereby incorporated by reference in its entirety). Predictions from each softmax output may be penalized by the cross-entropy function, and its sum across all tissue types may be back-propagated to update the parameters of the neural network. Training and testing of the model may be performed in a similar fashion as described, for example, by Leung et al. (Deep learning of the tissue-regulated splicing code, *Bioinformatics*, 2014; which is hereby incorporated by reference in its entirety). Briefly, data may be split into approximately five equal folds at random for cross validation (e.g., a 5-fold cross-validation). Each fold may contain a unique set of genes that are not found in any of the other folds. Three of the folds may be used for training, one of the folds may be used for validation, and one of the folds may be held out for testing. By selecting which fold is held out for testing, five models may be trained. The prediction of these five models on their corresponding test set may be used for performance assessment, as well as to estimate variances, for all the tasks analyzed in this work.

The validation set may be used for selection of hyperparameters. Examples of the selected hyperparameters for the models can be found in Example 13. A graphics processing unit (GPU) may be used to accelerate training and hyperparameter selection by randomly sampling the hyperparameter space.

Polyadenylation Site Preferences

For a given set of candidate polyadenylation sites, a prediction model may calculate feature vectors $x_1, \ldots, x_n$, for n candidate polyadenylation sites, and may use these to calculate a set of preferences $p_i, \ldots, p_n$, for the candidate polyadenylation sites. The prediction model may comprise a first computation module and a second computation module, as described elsewhere herein. A dataset of polyadenylation sites and the usage of the candidate polyadenylation sites may be used to adjust the parameters $\theta$ of the prediction model.

Polyadenylation sequence data and polyadenylation site usage data may be obtained. For example, polyadenylation sequence data may be obtained or derived from a reference genome, by sequencing deoxyribonucleic acid (DNA) or ribonucleic acid (RNA) of one or more bodily samples obtained from one or more subjects, or by performing modifications (e.g., incorporating one or more genetic aberrations) of such data. Such sequencing may be performed using next-generation sequencing (e.g., massively parallel sequencing or single molecule sequencing). A genetic aberration may be, for example, a single nucleotide variant (SNV) or an insertion or deletion (indel). Polyadenylation usage data may be obtained using genome annotations, complementary DNA (cDNA) and expressed sequence tag (EST) libraries, or by sequencing polyadenylated RNA of one or more bodily samples obtained from one or more subjects. For each of one or more genomic sequences, a set of candidate polyadenylation sites with corresponding measured preferences may be produced.

Next, training cases may be obtained. Each training case may correspond to a set of candidate polyadenylation sites that are identified in the sequence data. Each training case may comprise feature vectors $x_1, \ldots, x_n$, for the n candidate polyadenylation sites, obtained using the genomic sequence; and measured preferences $\hat{p}_1, \ldots, \hat{p}_n$ for the candidate polyadenylation sites, obtained using the polyadenylation site usage data. In some embodiments, the measured preferences reflect the proportions of transcripts that map to each of the set of candidate polyadenylation sites and sum to one, i.e., $\hat{p}_1 + \hat{p}_2 + \ldots + \hat{p}_n = 1$. The set of measured preferences corresponding to the candidate polyadenylation sites may be denoted by $\hat{p} = \hat{p}_1, \ldots, \hat{p}_n$, and the set of feature vectors $x_1, \ldots, x_n$ corresponding to the candidate polyadenylation sites may be denoted by $x = x_1, \ldots, x_n$.

Using the polyadenylation site feature vectors x, and a set of parameters $\theta$, the prediction model may calculate a set of preferences corresponding to the candidate polyadenylation sites, $p_1, \ldots, p_n$. Denoting these by p, where $p = p_1, \ldots, p_n$, the calculation performed by the prediction model may be denoted as $p \leftarrow f(x, \theta)$.

In some embodiments, the feature vector for the ith candidate polyadenylation site, $x_i$, encodes the RNA sequence of length m centered on the polyadenylation site. The nucleotides adenine (A), cytosine (C), guanine (G), and uracil (U) may be encoded as (1,0,0,0), (0,1,0,0), (0,0,1,0) and (0,0,0,1), respectively, and the encodings of the m nucleotides may be appended to form a binary sequence of length 4m. For example, for an RNA sequence GCAGCU3'GUUUCG (SEQ ID NO: 1), where 3' indicates the polyadenylation site, and a window of size m=4, the feature vector may be expressed by (0,1,0,0,0,0,0,1,0,0,1,0, 0,0,0,1). The prediction model may calculate the preferences $p_1, \ldots, p_n$ by first calculating a set of corresponding intermediate representations $r_1, \ldots, r_n$, each of which may comprise a numerical value. The intermediate representation for the ith candidate polyadenylation site may be calculated using the following linear summation:

$$r_i \leftarrow \theta_1 x_1 + \theta_2 x_2 + \ldots + \theta_{4m} x_{4m}.$$

where the subscripts $1, 2, \ldots, 4m$ index the elements of the binary sequences of length 4m, and each intermediate representation may comprise a sum of 4m terms. The intermediate representations may then be used to calculate the preferences as follows:

$$p_i \leftarrow \frac{\exp(r_i)}{\exp(r_1) + \exp(r_2) + \ldots + \exp(r_n)}, \text{ for } i = 1, \ldots, n.$$

The feature vectors may encode other features, such as the presence of certain patterns; a numerical representation of RNA secondary structure; and a numerical encoding of nucleosome positioning. The intermediate representation for each polyadenylation site may comprise a single numerical value or a vector of numerical values, and may be calculated using a linear summation as shown above, a multilayer neural network comprised of multiple layers of computations with nonlinearities, a recurrent neural network, or one of many other types of machine learning systems. The intermediate representations for the polyadenylation sites may be combined using different computational approaches, such as those described elsewhere herein, to calculate the preferences.

A set of initial training parameters $\theta$ may be generated, e.g., by using preset values, by using a random number generator, or by setting them using additional data. A goal of training may be to adjust the set of training parameters $\theta$ so that p and $\hat{p}$ are close for every training case. Denoting the index of the training case by j, the polyadenylation feature vectors, the preferences corresponding to the candidate polyadenylation sites calculated by the prediction model, and the measured preferences corresponding to the candidate polyadenylation sites may be denoted respectively by: $x^j, p^j, \hat{p}^j$. These feature vectors and calculated preferences may be initialized, e.g., by setting all initial values to 0 or 1.

A loss function $L(p^j, \hat{p}^j, \theta)$ may be evaluated for the calculated preferences and the measured preferences, for the current set of training parameters $\theta$. This loss function may depend on the parameters because the calculation of the preferences depends on the parameters, as described above. Examples of suitable loss functions include a negative cross entropy loss function, given by:

$$L = -\Sigma_{i=1}^{n} p_i \log \hat{p}_i$$

or a squared error loss function, given by:

$$L = 1/2 \Sigma i = 1^n (p_i - \hat{p}_i)^2,$$

but other loss functions may also be suitable.

A gradient-based learning procedure may be used to iteratively update the set of training parameters θ so as to decrease the total loss, as given by:

L=L($p_1$, $\hat{p}_1$, θ)+L($p_2$, $\hat{p}_2$, θ)+ . . . +L($p_T$, $\hat{p}_T$, θ), wherein T is the number of training cases. This may be iterated until a stopping criterion is satisfied. Examples of stopping criteria are that a pre-determined number of iterations have been performed, that a decrease in the total loss from one iteration to the next is below a pre-determined threshold, or that the total loss evaluated on a held-out validation set (e.g., a subset of the training data set) increases instead of decreases. By considering a gradient of the total loss with respect to a single parameter $$\frac{\partial L}{\partial \theta_j},$$

a learning rate α, and iteratively generating small updates in a direction of the gradient:

$$\theta_j^{k+1} \leftarrow \theta_j^k + \alpha \frac{\partial L}{\partial \theta_j^k}$$

in its direction, the loss function can be minimized. For each iteration, a parameter update may be obtained by differentiating the selected loss function (to obtain a differential) and numerically evaluating the differential. The minimization of the loss function may result in more accurate predictions as training progresses iteratively. This gradient-based learning procedure may be combined with a variety of standard techniques, such as batch gradient descent, minibatch learning, stochastic gradient descent, learning with dropout, momentum-based learning methods, and others.

A final prediction model may be generated comprising a final configuration of the set of training parameters θ, which may then be used to calculate the polyadenylation preferences for any set of polyadenylation site feature vectors. For training, it may be advantageous to alternate evaluation on randomized batches of training examples with parameter updates. As an example, a random set of training examples may be selected, the loss function may be evaluated based on this selected random set of training examples, gradients with respect to the model parameters may be computed, and the model parameters may be updated. This process may then be repeated with a different random set of training examples. As an example, a plurality of models can be trained such that each model generates a plurality of parameters and a prediction, and a plurality of predictions can be combined into a single prediction (e.g., by averaging).

Since the same model may be applicable to examples with any number n of candidate polyadenylation sites, it may be advantageous to either only select training examples with the same number of candidate polyadenylation sites in one batch, or to select them such that the number of candidate polyadenylation sites in the same batch are not too dissimilar.

Whenever a single batch of training examples contains cases with different numbers of candidate polyadenylation sites (e.g., a "ragged batch"), one or more decoy inputs may need to be added to the cases with fewer candidate polyadenylation sites, thereby making all cases equal (e.g., having equal numbers of candidate polyadenylation sites) for computational reasons (e.g., a "balanced batch"), as well as mask out the preferences outputs corresponding to the decoy inputs.

The calculations made by the prediction model may be efficiently implemented on a graphics processing unit (GPU) for efficient training and for application at test time.

A plurality of candidate polyadenylation sites may be identified in a genomic sequence (e.g., a human genome). The polyadenylation sites may comprise a contiguous segment of mRNA or DNA. The polyadenylation site may correspond to a possible start of a polyadenylation event in the human genome. The human genome may be obtained by sequencing mRNA or DNA of a bodily sample obtained from a subject.

The systems and methods described herein may comprise using trained algorithms to predict the utilization of a set of candidate polyadenylation. One or more polyadenylation site feature vectors may be calculated for each candidate polyadenylation site of the plurality of candidate polyadenylation sites. The polyadenylation site feature vectors may be calculated by performing calculations on (e.g., processing) an mRNA sequence (or alternatively, a DNA sequence corresponding to the mRNA sequence) data. Feature vectors $x_i$ for the ith candidate polyadenylation site may be obtained.

Each feature vector may comprise a vector of one or more features determined at least based on one or more nucleotide positions in the human genome. These features may be determined using other systems. A feature may be determined at least based on one or more nucleotides in the genomic sequence. In some embodiments, the at least one of the one or more nucleotides are located within about 50, 40, 30, 25, 20, 15, 10, or 5 nucleotides of the location in the genomic sequence of a polyadenylation site. For example, a feature may comprise a raw sequence at a nucleotide position that may be encoded using a 1-of-4 binary vector for each nucleotide in a set of possible nucleotides for the sequence type (e.g., mRNA or DNA). For an mRNA sequence, a set of possible nucleotides may comprise adenine, "A"; uracil, "U"; cytosine, "C"; or guanine, "G." For a DNA sequence, a set of possible nucleotides may comprise adenine, "A"; thymine, "T"; cytosine, "C"; or guanine, "G." For instance, a 1-of-4 binary vector [0, 1, 0, 0]$^T$ in an mRNA sequence may denote that a nucleotide located at a particular nucleotide position in the mRNA sequence is uracil, "U." For instance, a 1-of-4 binary vector [0, 1, 0, 0]$^T$ in a DNA sequence may denote that a nucleotide located at a particular nucleotide position in the DNA sequence is thymine, "T."

A feature may comprise a binary component (value). For example, a feature may comprise a binary value indicating the presence (e.g., value of 1) or absence (e.g., value of 0) of a certain sequence (e.g., a motif in a polyadenylation site). A feature may comprise categorical, integer, or real-valued components. For example, a feature may comprise an integer component such as a distance, in number of nucleotides, of a candidate polyadenylation site from a given genomic position.

A first computation module may be used to process a polyadenylation site feature vector to calculate a set of intermediate representations ($r_1$, $r_2$, . . . , $r_n$) corresponding to the plurality (n) of candidate polyadenylation sites. For each candidate polyadenylation site, a series of one or more structure computations may be performed on the feature vectors to determine an intermediate representation $r_i$ comprising one or more numerical values.

Each of the values in the set of intermediate representations may indicate a preference of a candidate polyadenylation site relative to the other candidate polyadenylation sites of the plurality, with higher preference values indicating a higher likelihood of being selected as an actual polyadenylation site in a polyadenylation process, and lower preference values indicating a lower likelihood of being selected as an actual polyadenylation site in a polyadenylation process. For instance, if each of the intermediate representations comprises a single numerical value and if the first candidate polyadenylation site has a largest intermediate representation among the set of intermediate representations corresponding to the plurality of candidate polyadenylation sites, then the first candidate polyadenylation site is the most likely to be selected (e.g., maximally preferred) as an actual polyadenylation site in a polyadenylation process.

Once the intermediate representations for all of the candidate polyadenylation sites have been determined, $r_1, r_2, \ldots, r_n$, they may be processed by a second computation module to produce a set of preferences, $p_1, p_2, \ldots, p_n$. Thus, a second computation module may be used to calculate a set of preferences $p_i$ ($p_1, p_2, \ldots, p_n$) for a selection of the ith candidate polyadenylation site among the plurality of candidate polyadenylation sites. This may be performed using a second computation module denoted by $p_1, p_2, \ldots, p_n \leftarrow h(r_1, r_2, \ldots, r_n)$, where h is a pre-determined function on a set of one or more intermediate representation values.

For example, the second computation module may be operable to normalize the ith preference for a candidate polyadenylation site by using an exponential function for h, by assigning:

$$p_i \leftarrow \frac{\exp(r_i)}{\exp(r_1) + \exp(r_2) + \ldots + \exp(r_n)},$$

where exp( ) is an exponential function or a numerical approximation of an exponential function. As another example, the second computation module may be operable to normalize the ith preference for a candidate polyadenylation site by using a rectified linear function for h, by assigning:

$$p_i \leftarrow \frac{relu(r_i)}{relu(r_1) + relu(r_2) + \ldots + relu(r_n)},$$

where relu( ) is a rectified linear function (e.g., whose function output is equal to its input if the input is positive, or is equal to zero otherwise). The second computation module may be operable to normalize the ith preference for a candidate polyadenylation site by using another type of function for h. This function may be a monotonic function to preserve order of preferences between a set of intermediate representation values and a set of preference values.

Each preference $p_i$ among the set of preferences ($p_1, p_2, \ldots, p_n$) may indicate a probability of selection of an ith candidate polyadenylation site among the plurality of candidate polyadenylation sites in a polyadenylation process. As such, a sum of the set of preferences may equal one (e.g., $p_1+p_2+\ldots+p_n=1$).

A maximally preferred candidate polyadenylation site may be identified among the plurality of candidate polyadenylation sites by selecting the candidate polyadenylation site with a largest value of preference $p_{max}$ among the set of preferences ($p_1, p_2, \ldots, p_n$).

A genomic sequence, as described elsewhere herein, may be constructed by hand or by a computer by combining sequences from different sources, including polyadenylated sequences. For example, a polyadenylated mRNA molecule may be reverse transcribed into a complementary DNA (cDNA) molecule, and the resulting cDNA molecule may be sequenced to obtain a polyadenylated sequence. This polyadenylated sequence may be mapped to a genome (e.g., a human genome) by hand or by a computer. There may be different ways of assembling, by hand or by a computer, a genomic sequence for the purposes described herein.

Effects of genetic variants on polyadenylation (e.g., on canonical polyadenylation sites and/or candidate polyadenylation sites) may be evaluated. To evaluate a genetic variant, the variant may be specified with respect to a reference sequence, which may be derived from, e.g., the genome, DNA sequencing, sequencing mRNA, or another approach. The variant may be specified by a sequential combination of one or more substitutions, insertions, and deletions with respect to the reference sequence. A substitution may be specified by a location in the reference sequence and the nucleotide (e.g., A, T, C, or G) that is substituted for the nucleotide at that location. An insertion may be specified by a location in the reference sequence and a nucleotide that is inserted right after the nucleotide at that location. A deletion may be specified by a location in the reference sequence at which a nucleotide has been removed from the sequence.

In some embodiments, the reference sequence is from the human genome. In some embodiments, the reference sequence is specified by a set of genomic coordinates. In some embodiments, the genetic variant is specified by a series of substitutions, insertions, and deletions in the genome, as indicated using the set of genomic coordinates.

The system may maintain a database of sequences along with canonical polyadenylation sites within the sequences. Canonical polyadenylation sites generally refer to polyadenylation sites that have been previously reported or identified using, e.g., genome annotations, cDNA and EST data, RNA-Seq data, or another approach. The sequences may be represented as strings (e.g., a sequence) of letters (e.g., representing nucleotides), as substrings from a reference genome (e.g., a human genome), as pointers or genomic coordinates in a reference genome (e.g., a human genome), or another approach.

The human genome may be used to represent the sequences. One or more genetic variants may be identified in a database of reference sequences (e.g., a human genome). Each of the one or more genetic variants may comprise one or more aberrant nucleotide positions in the human genome. A genetic variant may be selected from the group consisting of: a substitution at one or more nucleotide positions relative to a reference sequence (e.g., a single nucleotide variant (SNV) or a single nucleotide polymorphism (SNP)), an insertion at one or more nucleotide positions relative to a reference sequence, and a deletion at one or more nucleotide positions relative to a reference sequence. An insertion or a deletion may be referred to as an indel. A reference sequence may comprise a portion or entirety of a human genome. For example, a reference sequence may comprise a portion or entirety of a human reference genome (e.g., GRCh38). Genetic variants may be identified using one or more databases of reported variants. Genetic variants may be reported to occur in a cohort of individuals with common characteristics, such as healthy subjects, subjects with a disease state or disorder state, subjects previously diagnosed with a disease state or disorder state, or subjects previously treated for a disease state or disorder state.

The genetic variant may be mapped to canonical polyadenylation sites from a set of annotated polyadenylation sites. This mapping may be used to identify canonical polyadenylation sites that may be affected by the genetic variant and may include polyadenylation sites wherein the adjacent nucleotides within a window of size W (e.g., in units of nucleotide locations or bases) are altered by the genetic variant, or wherein the genetic variant alters nucleotides within a window of size W centered on other polyadenylation sites. Canonical polyadenylation sites may be identified by other approaches. Each canonical polyadenylation site may comprise a contiguous segment of mRNA or DNA, or a location within a contiguous segment of mRNA or DNA.

For a given genetic variant, a plurality of affected candidate polyadenylation sites may be identified. A candidate polyadenylation site may comprise a contiguous segment of mRNA or DNA. A set of candidate polyadenylation sites may comprise reported alternative polyadenylation sites. The plurality of candidate polyadenylation sites may include canonical polyadenylation sites that may be observed in polyadenylation, as determined by examining annotations or cDNA/EST data or RNA-Seq data. The plurality of candidate polyadenylation sites may include additional putative polyadenylation sites that the genetic variant may introduce.

It may be acceptable for the identification of putative polyadenylation sites to have a higher false positive rate than is required by downstream applications, because the machine learning system described elsewhere herein is capable of determining whether or not such identified putative polyadenylation sites are bona fide polyadenylation sites, thereby achieving a significantly lower false positive rate. In some embodiments, all nucleotide positions within some window of a reported PAS may be identified as putative polyadenylation sites and are included in the plurality of candidate polyadenylation sites.

For the plurality of candidate polyadenylation sites, feature vectors may be calculated using the reference sequence, as described elsewhere herein. The reference sequence may be processed to obtain feature vectors. The prediction model may be used to determine a set of preferences for the plurality of candidate polyadenylation sites, $p_1, p_2, \ldots, p_n$, as described elsewhere herein.

The genetic variant sequence (the reference sequence modified by the genetic variant) may be used to calculate modified feature vectors for the plurality of polyadenylation sites, as described elsewhere herein. The modified feature vectors for the ith candidate polyadenylation site may be denoted by $\tilde{x}_i$. The prediction model may be used to determine a set of modified preferences for the plurality of candidate polyadenylation sites, $\tilde{p}_1, \tilde{p}_2, \ldots, \tilde{p}_n$, as described elsewhere herein.

The preferences for the plurality of candidate polyadenylation sites may be compared to the modified preferences for the plurality of candidate polyadenylation sites to determine a quantified measure of an effect of the genetic variant. Examples of possible methods of calculating this quantified measure are described elsewhere herein.

As an alternative to comparing the set of preferences and the set of modified preferences when determining the quantified measure of the effect of the genetic variant, intermediate representations used in the calculations of the set of preferences and the set of modified preferences may be compared, as described elsewhere herein.

In some embodiments, for each candidate polyadenylation site in the plurality of candidate polyadenylation sites, the calculation $r_i \leftarrow f(x_i)$ of the intermediate representation within the first computation module is performed using a neural network, a deep neural network, a convolutional neural network, a recurrent neural network, a short-term long-term recurrent neural network, or another type of machine learning model. A convolutional or recurrent neural network may process the feature vectors separately, and the resulting hidden representation may be subsequently fed into another neural network. Alternatively, the feature vectors may be concatenated to form one feature vector, which may be processed by a convolutional or a recurrent neural network, or some other type of neural network. The feature vectors may be assembled in various ways for processing within the first computation module.

In some embodiments, modified feature vectors may be calculated. The modified feature vectors may comprise the one or more genetic variants for each of the plurality of candidate polyadenylation sites. The modified feature vectors may be calculated using a modified sequence of the genetic variant (e.g., substitution, insertion, or deletion applied to the reference sequence, which may be derived from the human genome). The modified feature vectors for the ith candidate polyadenylation site may be denoted by $\tilde{x}_i$. A tilde symbol ("~") may be used to denote a feature vector, an un-normalized preference, or a normalized preference that has been modified by a genetic variant.

A first computation module may be used to process a modified polyadenylation site feature vector to calculate a set of modified intermediate representations $\tilde{r}_i$ ($\tilde{r}_1, \tilde{r}_2, \ldots, \tilde{r}_n$) for the plurality of candidate polyadenylation sites. This calculation may be represented by $\tilde{r}_i \leftarrow f(\tilde{x}_i)$, i=1, ..., n, where f denotes the series of one or more structure computations that are performed on the modified feature vectors, and $\tilde{r}_i$ is the modified intermediate representation for the ith candidate polyadenylation site in the plurality of candidate polyadenylation sites.

The modified intermediate representations $\tilde{r}_1, \tilde{r}_2, \ldots, \tilde{r}_n$ in may be compared to the unmodified intermediate representations $r_1, r_2, \ldots, r_n$ to determine the effect of the genetic variant.

A second computation module may be used to calculate a set of modified preferences $\tilde{p}_i$ ($\tilde{p}_1, \tilde{p}_2, \ldots, \tilde{p}_n$) for the plurality of candidate polyadenylation sites. This calculation may be denoted by $\tilde{p}_1, \tilde{p}_2, \ldots, \tilde{p}_n \leftarrow h(\tilde{r}_1, \tilde{r}_2, \ldots, \tilde{r}_n)$, where h is a pre-determined function on one or more modified intermediate representations.

For example, the intermediate representations may each comprise a single numerical value and second computation module may be operable to normalize the ith preference for a candidate polyadenylation site by using an exponential function for h, by assigning:

$$\tilde{p}_i \leftarrow \frac{\exp(\tilde{r}_i)}{\exp(\tilde{r}_1) + \exp(\tilde{r}_2) + \ldots + \exp(\tilde{r}_n)},$$

where exp( ) is an exponential function or a numerical approximation of an exponential function. As another example, the second computation module may be operable to normalize the ith preference for a candidate polyadenylation site by using a rectified linear function for h, by assigning:

$$\tilde{p}_i \leftarrow \frac{relu(\tilde{r}_i)}{relu(\tilde{r}_1) + relu(\tilde{r}_2) + \ldots + relu(\tilde{r}_n)},$$

where relu( ) is a rectified linear function (e.g., whose function output is equal to its input if the input is positive, or is equal to zero otherwise). The second computation module may be operable to normalize the ith preference for a candidate polyadenylation site by using another type of function for h. This function may be a monotonic function to preserve order of preferences between a set intermediate representations and a set of preference values.

Each modified preference $\tilde{p}_i$ among the set of modified preferences ($\tilde{p}_1, \tilde{p}_2, \ldots, \tilde{p}_n$) may indicate a probability of selection of an ith candidate polyadenylation site among the plurality of candidate polyadenylation sites in a polyadenylation process. As such, a sum of the set of modified preferences may equal one (e.g., $\tilde{p}_1+\tilde{p}_2+ \ldots +\tilde{p}_n=1$).

A maximally preferred candidate polyadenylation site may be identified among the plurality of candidate polyadenylation sites by selecting the candidate polyadenylation site with a largest value of modified preference $\tilde{p}_{max}$ among the set of preferences ($\tilde{p}_1, \tilde{p}_2, \ldots, \tilde{p}_n$).

The effect of the genetic variant may be quantified by comparing the preferences of the plurality of candidate polyadenylation sites to the modified preferences. Based at least on this comparison, a quantitative measure may be generated and/or outputted. For example, if the maximally preferred candidate polyadenylation site in the modified and unmodified cases, $p_{max}$ and $\tilde{p}_{max}$, are different, a binary flag may be set to indicate a change.

If the intermediate representation is a single numerical value, a maximally preferred candidate polyadenylation site may be identified among the plurality of candidate polyadenylation sites by selecting the candidate polyadenylation site with a largest value of modified intermediate representation $\tilde{r}_{max}$ among the set of intermediate representations ($\tilde{r}_1, \tilde{r}_2, \ldots, \tilde{r}_n$).

A set of changes in preference $\Delta p_i$ ($\Delta p_1, \Delta p_2, \ldots, \Delta p_n$) may be calculated for the plurality of candidate polyadenylation sites. Each change in preference may be given by $\Delta p_i = \tilde{p}_i - p_i$, $\Delta p_i \in [-1, +1]$. Alternatively, each change in preference may be computed using $\Delta p_i = p_i \log (p_i/\tilde{p}_i)$, $\Delta p_i \in [-1, +1]$. The changes in preference may be computed using various methods. The set of changes in preference may comprise a change in preference for a canonical polyadenylation site $\Delta p_c$, $c \in \{1, \ldots, n\}$, which is of particular interest and importance, since any deviation from the canonical polyadenylation site pattern may be indicative of pathogenicity. The canonical polyadenylation site may be determined by examining genome annotations, examining cDNA libraries, or by other approaches.

A total probability mass change $\Delta P$ may be calculated between the set of preferences $p_i$ and the set of modified preferences $\tilde{p}_i$. The total probability mass change may be given by: $\Delta P = \frac{1}{2} \sum_{i=1}^{n} |\tilde{p}_i - p_i|$, $\Delta P \in [0, 1]$. In addition, a potentially cryptic polyadenylation site may be identified as a putative polyadenylation site (e.g., different from the canonical polyadenylation site) with a largest positive change in preference, given as:

$$\Delta p^{max} = \max_{i \neq c} \Delta p_i.$$

The preferences described above may be fed into another module that uses them to determine whether a specific disease is likely.

An effect of the one or more genetic variants on the set of candidate polyadenylation sites may be determined, by comparing the sets of intermediate representations $r_i$ ($r_1, r_2, \ldots, r_n$) and the sets of modified intermediate representations $\tilde{r}_i$ ($\tilde{r}_1, \tilde{r}_2, \ldots, \tilde{r}_n$).

Changes in one or more phenotypes in a subject may be identified by sequencing ribonucleic acid (RNA) molecules or deoxyribonucleic acid (DNA) molecules from a bodily sample obtained from the subject to produce a plurality of sequence reads and identifying one or more genetic variants in the plurality of sequence reads. Next, a set of polyadenylation sites associated with the one or more genetic variants may be identified. A set of modified preferences of the set of polyadenylation sites may then be determined, and a set of normalized preferences may also be determined using the reference sequence. These two sets of preferences may be compared to identify or detect changes in one or more phenotypes in the subject. For example, the changes in one or more phenotypes in the subject may be identified or detected at a probability of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or greater.

By determining a set of preferences of the set of polyadenylation sites corresponding to a polyadenylation site associated with a genetic variant, the effect of the genetic variant may be determined as described elsewhere herein. This effect of the genetic variant may be used to identify changes in one or more phenotypes in the subject at a probability of at least about 50%, e.g., by performing correlation studies of cohorts of subjects with reported genetic variants (e.g., DNA mutations) by comparing the changes in preferences to reported changes in one or more phenotypes (e.g., diseases or disorders). The probability may indicate a likelihood that a subject with the genetic variant is exhibiting, may exhibit in the future, or is expected to exhibit the change in one or more phenotypes. The probability may be at least about 50%, 55%, 60%, 65%, 70%, 75%, 80%, 85%, 90%, 91%, 92%, 93%, 94%, 95%, 96%, 97%, 98%, or 99%.

A machine learning algorithm may be used to identify the set of polyadenylation sites. The set of polyadenylation sites may comprise one or more polyadenylation sites reported to be associated with one or more polyadenylated mRNA sequences.

The RNA molecules may be subjected to reverse transcription (e.g., RT) and/or reverse transcription polymerase chain reaction (e.g., RT-PCR) to generate complementary DNA (cDNA) molecules. The cDNA may then be sequenced to produce the plurality of sequence reads. The RNA molecules may be messenger RNA (mRNA).

A library of probes may be generated to enrich for a set of polyadenylation sites in a nucleic acid sample of a subject. The set of polyadenylation sites may be generated using a preference computation module, as described elsewhere herein, and may correspond to genetic variants in the nucleic acid sample. The set of polyadenylation sites may identify changes in one or more phenotypes in the subject at a probability of at least about 90%. The probability may be at least about 55%, 60%, 65%, 70%, 75%, 80%, 85%, 90%, 91%, 92%, 93%, 94%, 95%, 96%, 97%, 98%, or 99%. The set of polyadenylation sites may comprise one or more polyadenylation sites reported to be associated with one or more polyadenylation events.

Computer Systems

The present disclosure provides computer systems that are programmed to implement methods of the disclosure. FIG.

2 shows a computer system 201 that is programmed or otherwise configured to determine effects of a genetic variant on a set of polyadenylation sites. The computer system 201 can regulate various aspects of the present disclosure, such as, for example, determining a set of preferences of a plurality of candidate polyadenylation sites. The computer system 201 can be an electronic device of a user or a computer system that is remotely located with respect to the electronic device. The electronic device can be a mobile electronic device.

The computer system 201 includes a central processing unit 205 (CPU, also "processor" and "computer processor" herein), which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220, and peripheral devices 225 are in communication with the CPU 205 through a communication bus (solid lines), such as a motherboard. The storage unit 215 can be a data storage unit (or data repository) for storing data. The computer system 201 can be operatively coupled to a computer network 230 ("network") with the aid of the communication interface 220. The network 230 can be the Internet, an internet and/or extranet, or an intranet and/or extranet that is in communication with the Internet. The network 230 in some cases is a telecommunication and/or data network. The network 230 can include one or more computer servers, which can enable distributed computing, such as cloud computing. The network 230, in some cases with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 201 can be included in the circuit. In some cases, the circuit is an application specific integrated circuit (ASIC).

The storage unit 215 can store files, such as drivers, libraries, and saved programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user. Examples of remote computer systems include personal computers (e.g., portable PC), slate or tablet PC's (e.g., Apple® iPad, Samsung® Galaxy Tab), telephones, smartphones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210 or electronic storage unit 215. The machine executable or machine readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 201 can include or be in communication with an electronic display 235 that comprises a user interface (UI) 240 for providing, for example, an approach for user selection of a monotonic function. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 205. The algorithm can, for example, determine a set of preferences of a plurality of candidate polyadenylation sites.

Formulations and Kits

The present disclosure provides formulations configured to administer compositions provided herein. A composition of the present disclosure (e.g., an antisense oligonucleotide) may be administered to a subject, such as for therapeutic purposes. The composition may be included in a formulation with a therapeutically effective amount of the composition. The formulation may include one or more excipients (e.g., a flavorant, colorant, buffer, preservation agent, etc.).

The present disclosure provides kits comprising a composition of the present disclosure and instructions usable by a user to administer the composition to a subject. The user may be the subject or a healthcare provider of the subject. The instructions may direct the user to administer the composition (e.g., in a formulation) to the subject at a given dosing regimen.

EXAMPLES

The examples below are illustrative and non-limiting with respect to various aspects and embodiments of the present disclosure. Features illustrated in these examples may be applied to other examples and implementations.

Example 1—Polyadenylation Site Selection

The performance of a model to predict the likelihood that a PAS is selected for cleavage and polyadenylation against a competing site in the same gene is shown in Table 1. These are the tissue-specific relative strength predictions for pairs of PAS which are shown in FIG. 1. Performance is assessed using the area under the receiver-operator characteristic (ROC) curve (AUC) metric on held-out test data. To compare the models' performance against a baseline, a logistic regression (LR) classifier is also trained, which is essentially the Feature-Net with hidden layers removed. Predictions from the model based on the Conv-Net architecture may be consistently the best performer. There is sizable performance gain observed from using the neural network models compared to the logistic regression classifier.

TABLE 1

PAS selection performance between competing sites in different tissues.

| | AUC | | |
|---|---|---|---|
| Tissue Type | LR | Feature-Net | Conv-Net |
| Brain | 0.826 ± 0.010 | 0.869 ± 0.007 | 0.895 ± 0.005 |
| Breast | 0.825 ± 0.006 | 0.862 ± 0.003 | 0.886 ± 0.004 |
| ES Cells | 0.849 ± 0.006 | 0.898 ± 0.002 | 0.911 ± 0.006 |
| Ovary | 0.830 ± 0.009 | 0.873 ± 0.006 | 0.895 ± 0.003 |
| Skeletal Muscle | 0.828 ± 0.006 | 0.872 ± 0.005 | 0.893 ± 0.004 |
| Testis | 0.787 ± 0.007 | 0.828 ± 0.005 | 0.856 ± 0.007 |
| B Cells 1 | 0.838 ± 0.005 | 0.880 ± 0.005 | 0.896 ± 0.004 |
| B Cells 2 | 0.832 ± 0.004 | 0.880 ± 0.008 | 0.893 ± 0.007 |
| All | 0.824 ± 0.005 | 0.866 ± 0.004 | 0.889 ± 0.003 |

For the more general task of predicting which PAS may be selected in a gene with multiple sites, the model is applied to all PAS in the 3'-UTR of each gene. A score for each site is computed from the logits (the output of the PAS strength predictor shown in FIG. 1), where a larger value suggests that the site is more likely to be selected. The target is defined by the PAS in each gene which has the most measured reads in the 3'-Seq data. The metric reported here is the prediction accuracy, or the percentage of genes in which the model has correctly predicted the PAS that has the most reads. This is shown in Table 2 for genes with two to six sites, averaged across all tissues. The number of genes used in this evaluation is 2270, 2043, 1745, 1364, and 1163, respectively, where a gene is included only if at least one of its sites has more than 10 reads.

TABLE 2

PAS selection performance in genes with 2 to 6 sites.

| | Accuracy (%) | | |
|---|---|---|---|
| Number of Sites | LR | Feature-Net | Conv-Net |
| 2 | 79.6 | 82.5 | 83.5 |
| 3 | 68.3 | 73.0 | 75.5 |
| 4 | 58.9 | 64.4 | 69.8 |
| 5 | 55.6 | 62.8 | 64.0 |
| 6 | 48.5 | 56.4 | 59.7 |

Figure 3A:
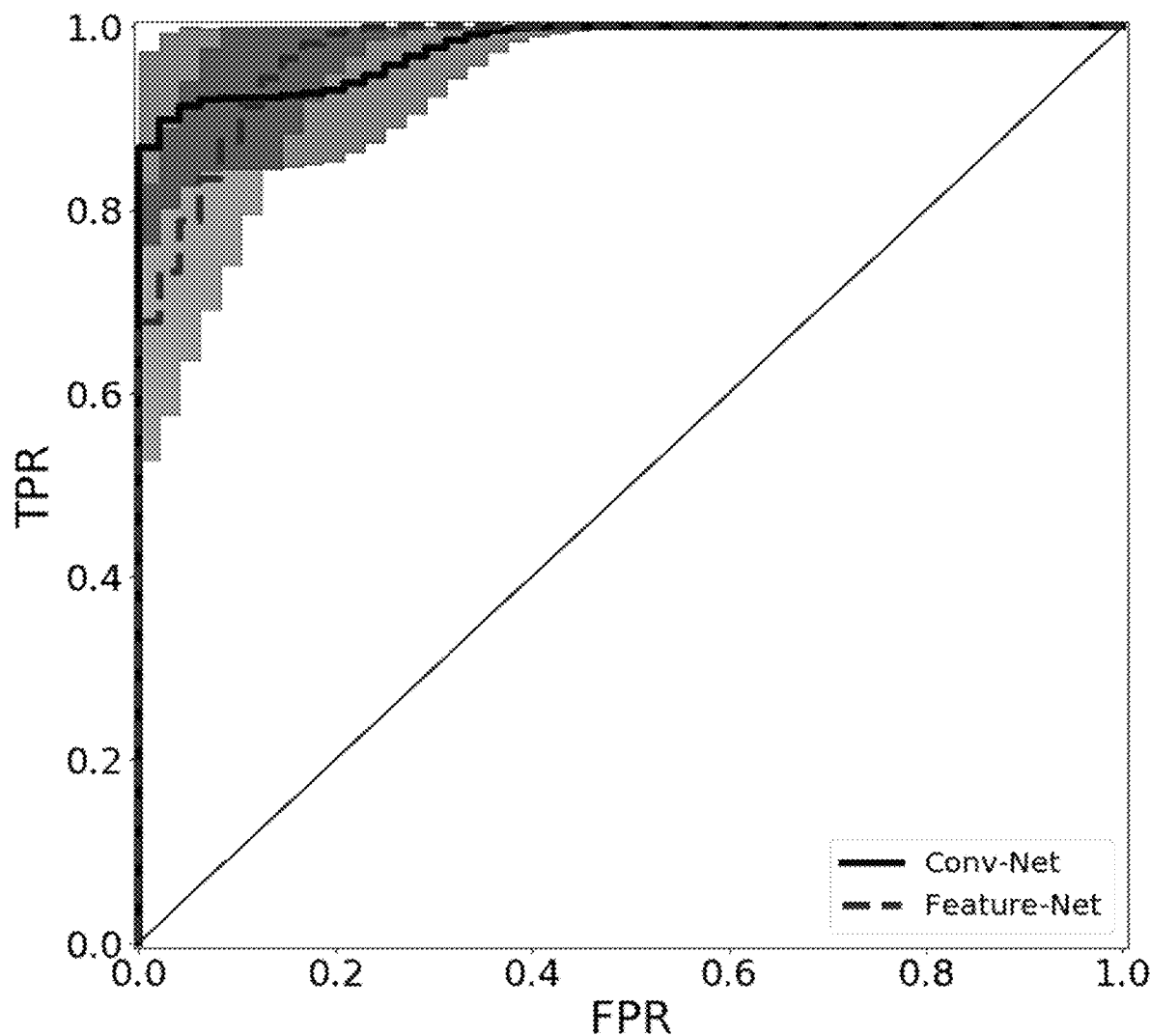
FIGS. 3A and 3B illustrate classification performance of ClinVar variants near polyadenylation sites.
Figure 3B:
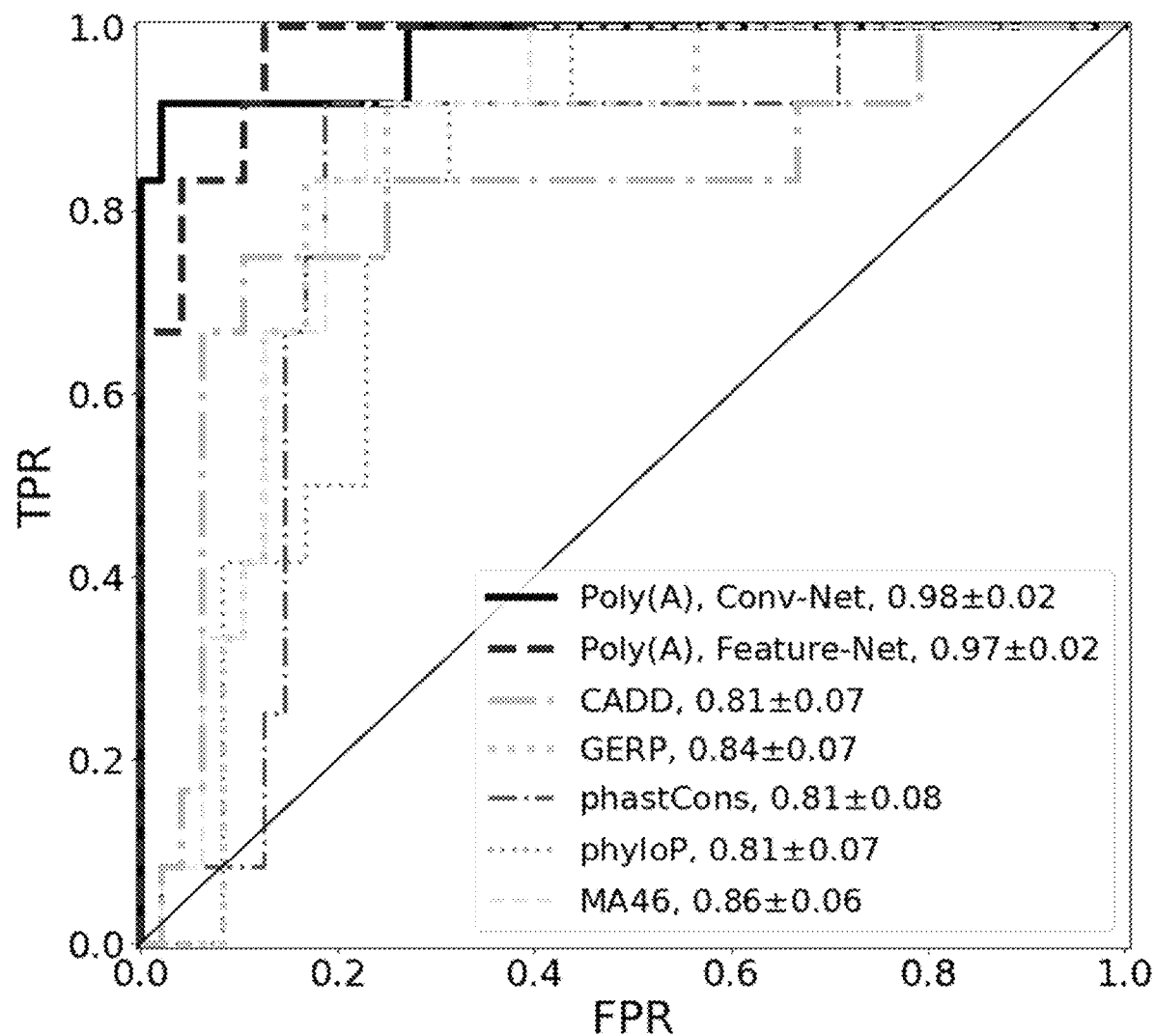

FIGS. 3A and 3B illustrate classification performance of ClinVar variants near polyadenylation sites, including ROC curves comparing the variant classification performance of the Conv-Net and the Feature-Net (FIG. 3A), wherein the shaded region shows the one standard deviation zone computed by bootstrapping, and ROC curves comparing performance of a model disclosed herein against other predictors (FIG. 3B). AUC values are shown in the figure legend.

Example 2—Pathogenicity Prediction of Polyadenylation Variants

An advantage of the model disclosed herein is that the PAS strength predictor can be used to characterize individual sites based only on the input sequence. This model is evaluated for suitability and performance of use for pathogenicity predictions. The basic approach comprises applying the model to the 200-nucleotide sequence associated with a PAS from the reference genome to first generate a prediction of its strength, and then performing another prediction when one or more nucleotides in the sequence are altered. A difference is then computed between the reference prediction and the variant prediction. Since there are eight predictions, one for each tissue, the largest difference is taken as the score to assess pathogenicity. A similar approach can be applied to splicing variants (as described, for example, by Xiong et al., The human splicing code reveals new insights into the genetic determinants of disease, *Science*, 2014; which is hereby incorporated by reference in its entirety). A postulate may be that if a variant causes a large change to the strength of a PAS, this can change the relative abundance of differentially 3'-UTR terminated transcripts that deviate from normal, potentially indicating disease associations.

To evaluate the efficacy of this approach, variants that overlap with the PAS atlas (within 100 bases on either side of an annotated PAS) are extracted from the ClinVar database, as described, for example, by Landrum et al. (ClinVar: public archive of relationships among sequence variation and human phenotype, *Nucleic Acids Res.*, 2014), which is hereby incorporated by reference in its entirety. Some of these variants overlap with the terminal exon (e.g., missense mutations) and are removed. There are 12 variants that are labeled as pathogenic (CLNSIG=5) and 48 that are labeled as benign (CLNSIG=2). FIG. 3A shows the ROC curve for this classification task. The model can predict pathogenic variants from benign ones with an AUC of 0.98±0.02 and 0.97±0.02, for the Conv-Net and Feature-Net respectively, both with a p-value of less than $1\times10^{-8}$. Even though the AUCs are essentially identical for both models, there is a clear advantage in the performance characteristic of the Conv-Net: it outperforms in the low false positive rate region where variant classification matters. For these predictions, an input of zero is used for the position feature of the strength model, since each variant is not analyzed with respect to neighboring sites. However, in general, it may be advantageous to incorporate this information. For example, a variant may cause a large change in a nearby PAS, but if there is a much stronger neighboring PAS in the same gene, the effects of the variant may be dwarfed by this neighbor, and therefore not have any significant mechanistic effects.

Further, a comparison of the model is evaluated with four phylogenetic conservation scoring methods: Genomic Evolutionary Rate Profiling (GERP) (as described, for example, by Cooper et al., Distribution and intensity of constraint in mammalian genomic sequence, *Genome Res.*, 2005; which is hereby incorporated by reference in its entirety), phastCons (as described, for example, by Siepel et al., Evolutionarily conserved elements in vertebrate, insect, worm, and yeast genomes, *Genome Res.*, 2005; which is hereby incorporated by reference in its entirety), phyloP (as described, for example, by Pollard et al., Detection of nonneutral substitution rates on mammalian phylogenies, *Genome Res.*, 2010; which is hereby incorporated by reference in its entirety), and the 46 species multiple alignment track from the UCSC genome browser (as described, for example, by Blanchette et al., Aligning multiple genomic sequences with the threaded blockset aligner, *Genome Res.*, 2004; which is hereby incorporated by reference in its entirety). In addition, the predictions are compared with Combined Annotation-Dependent Depletion (CADD), a tool which scores the deleteriousness of variants (as described, for example, by Kircher et al., A general framework for estimating the relative pathogenicity of human genetic variants, *Nat. Genet.* 2014; which is hereby incorporated by reference in its entirety). Overall, as shown in FIG. 3B, the pathogenicity score from the model described herein compares favorably, even though it is not explicitly trained for this task. In addition, although the model performs well for this ClinVar dataset, in general, a large difference in PAS strength does not necessarily imply pathogenicity, which is a phenotype that can be many steps downstream of 3'-end processing.

Figure 4:
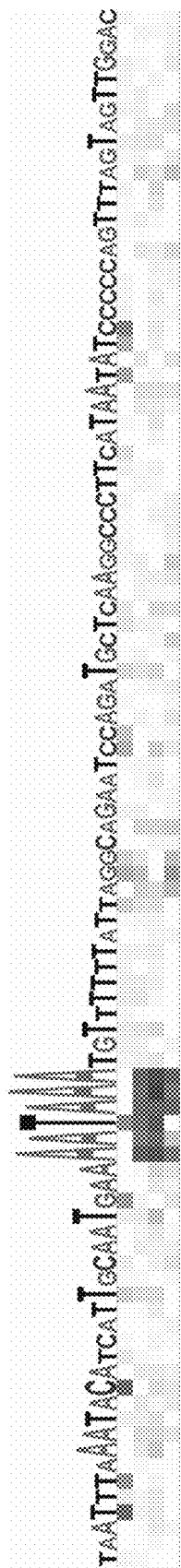
FIG. 4 illustrates a mutation map of the genomic region chr1: 5,246,678-5,246,777. Figure discloses SEQ ID NO: 6.

The model described herein can also be used to search for potential variants that may affect the regulation of polyadenylation. To visualize this approach, the model is applied and a mutation map is generated (as described, for example, by Alipanahi et al., Predicting the sequence specificities of DNA- and RNA-binding proteins by deep learning, *Nat. Biotechnol.*, 2015; which is hereby incorporated by reference in its entirety) to a 100-nucleotide sequence in the human genome, where a ClinVar mutation that affects the polyadenylation signal is associated with β-thalassemia (as described, for example, by Rund et al., Two mutations in the beta-globin polyadenylylation signal reveal extended transcripts and new RNA polyadenylylation sites, *Proc. Natl. Acad. Sci. U.S.A*, 1992; which is hereby incorporated by reference in its entirety). FIG. 4 illustrates a mutation map of the genomic region chr11: 5,246,678-5,246,777. Each square represents a change in the model's score if the original base is substituted. The substituted base is represented in each row in the order 'ACGT'. Different shades or colors can be used to denote mutations that may increase or decrease the likelihood (e.g., preference) of the PAS for cleavage and polyadenylation. As shown in FIG. 4, the polyadenylation signal is identified as an important region relative to other bases in the sequence.

Example 3—Polyadenylation Site Discovery

A model is trained by centering the input sequence around a PAS at the cleavage site. If a PAS is off-center of the 200-nucleotide input sequence, or when no PAS is present, then the predicted PAS strength of the sequence may be small, due to the lack of sequence elements necessary for cleavage and polyadenylation. Alternatively, if the output of the PAS strength predictor is large, it may suggest that a PAS is present and is positioned near the center of the input sequence. The model may be evaluated for suitability of translation across the genome to find potential PAS. The model disclosed herein may not be explicitly trained for this purpose.

To illustrate an example of a predicted PAS track, a section of the human genome is selected and the Conv-Net strength model is applied to the section in a base-by-base manner (as described, for example, in Example 10). The average strength prediction from all eight tissues, without application of any filtering or thresholding, is shown. For this example, a region of the genome with multiple PAS is chosen, where there are differences between annotation sources.

The set of predicted peaks labeled region A are present in all annotation sources. It is not a single sharp peak, indicating that various PAS are possible in that region. This agrees with the GENCODE Poly(A) track, which indicates that there are two peaks in this region, as well as 3'-Seq, which shows that there are RNA-Seq reads that map across a broad region for various tissues. As discussed elsewhere herein, the location for cleavage and polyadenylation is not exact. Region B is less well-defined, is weaker, and approximately aligns with the predicted positions from another PAS predictor (as described, for example, by Cheng et al., Prediction of mRNA polyadenylation sites by support vector machine, *Bioinformatics*, 2006; which is hereby incorporated by reference in its entirety), as well as the muscle track from PolyA-Seq (in light gray). Finally, a small peak is observed in Region C, predicted to be a very weak PAS, which is present in PolyA-Seq. Note that the model is trained only from 3'-Seq reads and has no knowledge of RNA-Seq information from other datasets or other annotation sources.

To assess the model's ability in discovering PAS, a dataset is created with positive and negative examples to assess its classification performance. Since there may be no general consensus regarding proper criteria to construct negative sequences or a standardized dataset for this task, the evaluation dataset is defined based on annotations and reads from 3'-Seq. Positive targets include annotated PAS in the 3'-UTR that have 10 or more reads. Since generally it may not be appropriate to simply use random genomic sequences or locations for the negative set, the two immediately adjacent genomic regions near a PAS are extracted to ensure that both the negative and positive sequences have similar compositions (as described, for example, in Example 11). Each sequence is fed as input into the strength predictor, and the outputs from all tissues are averaged into a single value which is used for classification. The positional information of the sequence is not used (i.e., it has a position feature of zero). The AUC to classify sequences with PAS from negative sequences for the LR, Feature-Net, and the Conv-Net are measured as 0.887±0.003, 0.895±0.004, and 0.907±0.004, respectively. Of the negative sequences, 19% contain one of the two canonical polyadenylation signals (AAUAAA and AUUAAA), and 74% contain at least one of the reported polyadenylation signals (as described, for example, in Example 8), indicating the model can distinguish real PAS from background. It does not simply look for the presence of polyadenylation signals to detect PAS in the genome.

There may be a relatively smaller difference in the AUCs for all models, such as between the Conv-Net and the logistic regression model, compared to previous tasks, which differ more drastically in performance. Identification of PAS from the genome is a simpler problem, characterized by the presence of features that are generally well-documented. For such tasks, a logistic regression classifier may be sufficient. On the other hand, predicting the strength of a PAS given its sequence may be more complex. Instead of a binary classification problem, a strength predictor may need to quantify a PAS by integrating its genomic signature, and predict how it compares with another site, which may also contain all the core polyadenylation signatures, but differ in other ways with respect to its sequence. This observation is supported by the larger differences in the models' performance to the PAS selection problems in Table 1 and Table 2, which require strength quantification.

Example 4—Predicting the Effect of Oligonucleotide Treatment

Anti-sense oligonucleotides therapies may include targeting RNAs via complementary base pairing, and can modulate RNA function by blocking the access of cellular machinery to the RNA. Application of this approach is demonstrated in the 3'-UTR, where oligonucleotides targeting polyadenylation signals and sites modulated the abundance of an mRNA (as described, for example, by Vickers et al., Fully modified 2' MOE oligonucleotides redirect polyadenylation, *Nucleic Acids Res.*, 2001; which is hereby incorporated by reference in its entirety). Based on this, the utility of the model disclosed herein is shown to provide an in-silico evaluation of oligonucleotides targeting regions near the PAS.

Figure 5:
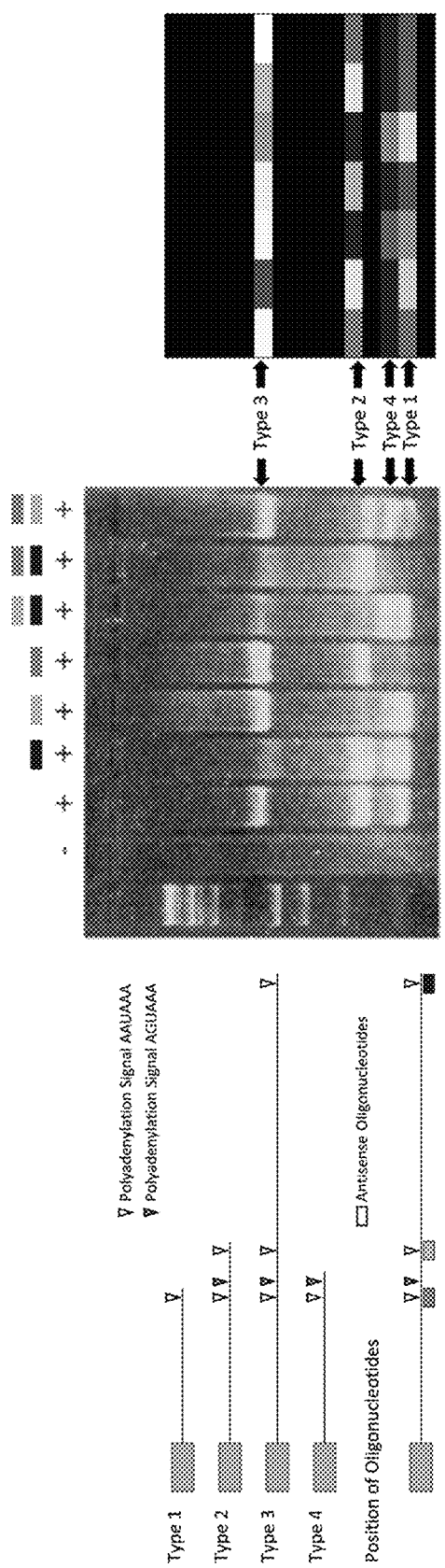
FIG. 5 illustrates an example of predicting the effect of an antisense oligonucleotide experiment.

Three distinct forms of the transcript (Type 1, Type 2, and Type 3) are described in the study. A schematic of the E-selectin mRNA and the position of the polyadenylation signal, along with the targeted region of the oligonucleotides used is shown in FIG. 5 (left). All three forms harbor the canonical polyadenylation signal AAUAAA. A non-canonical polyadenylation signal AGUAAA is also present between the Type 1 and Type 2 cleavage site, which is selected when the corresponding signals from Type 1 and Type 2 are blocked. Here, it is referred to as the Type 4 form of the transcript.

According to the study, Type 3 is by far the dominant form of the transcript, followed by Type 1 and Type 2 (no differentiation is reported between them). Type 4 is the least common. Using the model, the predicted strengths for the corresponding PAS for Type 1 to 4 transcripts are respectively: −0.242, −0.420, 0.020, −0.765. These values do not account for the position of the PAS. If the relative positions of the 4 PAS are provided to the model, then the strengths become: −0.242, −0.170, 0.606, −0.584 (where Type 1 is assumed to be in position zero). These predictions match the observed abundances of this mRNA from the study.

The Vickers et al. study performs a non-quantitative RT-PCR to assess the abundance of isoforms by administering different combinations of oligonucleotides targeting select regions of the transcript. To simulate this, the same regions of the input sequence complementary to the oligonucleotides are blocked by replacing the nucleotides with an N base, and the resulting strengths of each PAS are predicted. The results are shown in FIG. 5, where predicted PAS strength is shown and arranged in an image to match the gel from the Vickers et al. study (right), simulating the effects of blocked nucleotides due to oligonucleotide treatment. A figure from the Vickers et al. study is reproduced and shown for ease of comparison (left). The oligonucleotides applied are shown on top of each column. Each column is scaled such that the sum of the intensities of each column is constant, but otherwise, no additional processing is performed. The Vickers et al. study does not provide values from RT-PCR that permit quantitatively comparison with the output of our model, but qualitatively, patterns of polyadenylation are generally captured. Note that the Vickers et al. study mentions that Type 1 and 2 transcripts are shorter and therefore more efficiently amplified by PCR, and thus appear brighter than expected compared to Type 3. This experimental bias does not affect the simulated RT-PCR results shown in FIG. 5.

Example 5—Effect of Genomic Features on the Model's Predictions

To understand how different features contribute to performance, models are trained using only individual feature groups. Table 3 shows each model's classification performance. Even though the polyadenylation signals are generally considered to be a main signature of PAS, they only partially account for the predictive performance for PAS selection compared to the full feature set. Overall, n-mer features are major contributors to the Feature-Net's performance, which is sufficiently rich to capture many motif patterns. Each feature group may have a different number of features (as described, for example, in Example 8), and therefore individual features in the larger feature groups may contribute only weakly, but as a whole affect predictions considerably. Position alone may have poor predictive capability, even though it has been suggested to be a key feature in determining whether a PAS is used for tissue-specific regulation. Further, an investigation is conducted on the uniqueness of each feature group, by training models with all features minus each feature group from Table 3. Removing the polyadenylation signals from the feature set reduces the performance from 0.866±0.004 to 0.840±0.008. All other groups, when removed, do not significantly reduce the performance of the model compared to the full feature set. This suggests that many features are redundant, and if removed, can be compensated by features in another group.

TABLE 3

Comparison of Feature-Net PAS selection performance between competing sites using feature subsets.

| Feature Group | AUC |
| --- | --- |
| All | 0.866 ± 0.004 |
| Poly (A) Signal | 0.728 ± 0.004 |
| Position | 0.553 ± 0.004 |
| Cis-Elements | 0.608 ± 0.009 |
| RBP Motifs | 0.676 ± 0.009 |
| Nucleosome Occupancy | 0.656 ± 0.006 |
| 1-Mers | 0.762 ± 0.004 |
| 2-Mers | 0.794 ± 0.002 |
| 3-Mers | 0.817 ± 0.004 |
| 4-Mers | 0.833 ± 0.005 |

To see the contributions of individual features, the gradient of the output of the neural network with respect to the input feature vector of the neural network is computed. This is referred to as the feature saliency of a prediction of the neural network, and the gradients of features with large magnitudes can be interpreted as those that need to change the least to affect the prediction the most (as described, for example, by Simonyan et al., Deep inside convolutional networks: visualising image classification models and saliency maps, Proc. of the Int. Conf on Learn. Representations, 2014; which is hereby incorporated by reference in its entirety). For this, the feature saliency values of each of the sites in the test set are computed, and the features that on average have the largest magnitude are selected. Table 4 shows the top 15 features computed using this method and the direction in which the feature affects the strength of a PAS, where an up arrow indicates that the effect is positive.

TABLE 4

Top 15 features of the Feature-Net, and the direction in which each feature can increase (↑) or decrease (↓) the strength of a polyadenylation site.

| Rank | Region | Feature Name | Direction |
| --- | --- | --- | --- |
| 1 | 5'-3' | PolyA Signal. AAUAAA | ↑ |
| 2 | — | Log distance between PAS | ↑ |
| 3 | 5'-3' | PolyA Signal, AUUAAA | ↑ |
| 4 to 15 | 5'-3' | 1-mer, C | ↓ |
| | 5'-3' | 1-mer, U | ↑ |
| | 5'-3' | 2-mer, AG | ↓ |
| | 3'-5' | 2-mer, CA | ↓ |
| | 3'-5' | 3-mer, AAA | ↑ |
| | 5'-3' | 3-mer, UGU | ↑ |
| | 5'-5' | 3-mer, UGU | ↑ |
| | 3'-5' | 4-mer, AAAA | ↑ |
| | 5'-5' | Cleavage Factor Im, UGUA | ↑ |
| | 5'-3' | PolyA Signal, CAAUAA | ↑ |
| | 5'-3' | PolyA Signal. AUAAAG | ↑ |
| | 5'-5' | PolyA Signal. AGUAAA | ↑ |

The top three features are consistent for all tissue types. Other features vary slightly between tissues and are grouped together unordered. As expected, the two most common canonical polyadenylation signals are the top features which increase the strength of a PAS. The log distance between PAS is also deemed to be important. Some features in this list are consistent with mechanisms of core elements previously reported to be involved in cleavage and polyadenylation, including the upstream UGUA motif which the cleavage factor Im complex binds to, and a GU-rich sequence near the polyadenylation site. The genomic context upstream of the PAS appears to be more important, as most of the top features are in either the 5'-5' and 5'-3' region. Three of the features may reduce the strength of a PAS. They are the frequencies of C and AG nucleotides in the upstream region and the CA nucleotides downstream of the cleavage site, the latter of which is consistent with reported results that the C-terminal domain of RNA polymerase II interacts with CA-rich RNA sequences, and has been reported to play a role in inhibiting polyadenylation (as described, for example, by Kaneko and Manley et al., The Mammalian RNA Polymerase II C-Terminal Domain Interacts with RNA to Suppress Transcription-Coupled 3' End Formation, *Mol. Cell.*, 2005; which is hereby incorporated by reference in its entirety).

Example 6—Determining Tissue-Specific Polyadenylation Features

Given that APA is used to achieve tissue-specific gene expression, the model's ability to provide insights to this phenomenon is evaluated. Computational approaches to address this problem have been previously reported. For example, an A-rich motif has been reported to be enriched in brain-specific PAS (as described, for example, by Hafez et al., Genome-wide identification and predictive modeling of tissue-specific alternative polyadenylation, *Bioinformatics*, 2013; which is hereby incorporated by reference in its entirety). For example, the position of a PAS relative to another PAS and its position in the gene have been reported to be the strongest indicator of whether it is tissue-specific (as described, for example, by Weng et al., Poly(A) code analyses reveal key determinants for tissue-specific mRNA alternative polyadenylation, *RNA*, 2016; which is hereby incorporated by reference in its entirety). The computational models for both these works are trained to directly classify whether a PAS is tissue-specific. To be consistent with the methodology presented in this work, the models described herein are analyzed without re-training them.

The set of tissue-specific and constitutive PAS described, for example, by Weng et al. are selected, and the Feature-Net is applied to this set of PAS to generate predictions. To determine which feature is associated with tissue-specific PAS, the gradient-based method described in Example 5 is used to examine the top 200 most confident predictions for tissue-specific PAS, where the model predicts that at least one of the tissue outputs is considerably different than the rest, and for constitutive PAS, where the model predicts that all tissue outputs do not differ significantly. The magnitude of the gradients is then analyzed to see which features have a statistically greater effect on tissue-specific PAS compared to constitutive PAS. Statistical significance is determined by a permutation test by shuffling the predictions indicating whether a PAS it tissue-specific or constitutive. Applying a conservative p-value of 0.05/1506 (number of features)=3× $10^{-5}$, a set of 15 features is found to be associated with the model's ability to predict tissue-specific PAS, as shown in Table 5. In the column indicating direction, an up arrow indicates the presence of the feature makes the site more likely to be tissue-specific, and vice versa.

TABLE 5

Features associated with prediction of tissue-specific polyadenylation sites, and whether the presence of the feature makes a polyadenylation site more (↑) or less (↓) tissue-specific.

| Region | Feature Name | P-value | Direction |
|---|---|---|---|
| 5'-5' | 4-mer, UUGU | $8.0 \times 10^{-11}$ | ↓ |
| 3'-3' | 3-mer, UUG | $9.9 \times 10^{-09}$ | ↑ |
| 3'-3' | 4-mer, CCCC | $5.7 \times 10^{-08}$ | ↓ |
| 5'-5' | 3-mer, UGU | $6.8 \times 10^{-08}$ | ↓ |
| 3'-3' | 4-mer, UCCC | $1.1 \times 10^{-07}$ | ↓ |
| 5'-5' | 4-mer, CGGC | $1.0 \times 10^{-06}$ | ↓ |
| 5'-5' | Cis-element, UUUGUA | $1.7 \times 10^{-06}$ | ↓ |
| 5'-5' | Cleavage Factor Im, UGUA | $2.2 \times 10^{-06}$ | ↓ |
| 5'-5' | 3-mer, UUG | $3.4 \times 10^{-06}$ | ↓ |
| 5'-5' | 3-mer, AUC | $7.4 \times 10^{-06}$ | ↑ |
| 3'-3' | 3-mer, UCC | $1.2 \times 10^{-05}$ | ↓ |
| 5'-5' | 2-mer, UC | $1.7 \times 10^{-05}$ | ↑ |
| 5'-5' | 4-mer, AUCC | $1.9 \times 10^{-05}$ | ↑ |
| 5'-5' | 2-mer, UU | $2.0 \times 10^{-05}$ | ↓ |
| 3'-3' | 3-mer, CCU | $2.1 \times 10^{-05}$ | ↓ |

All but one of the entries in the table describe features that are in the 5'-5' and 3'-3' region, that is, most of them are located away from the cleavage site (as described, for example, in Example 8). Various G/U-rich features top the list, where its position upstream suggests the PAS is more likely to be constitutive, but if downstream, the PAS is more likely to be tissue specific. Polyadenylation signals are absent from the list. No hexamers other than UUUGUA are found, which has been reported as a feature by statistical analysis (as described, for example, by Hu et al., Bioinformatic identification of candidate cis-regulatory elements involved in human mRNA polyadenylation, *RNA*, 2005; which is hereby incorporated by reference in its entirety). However, no association of this hexamer with tissue-specific polyadenylation has been previously reported. Given that the model only sees sequences from +/-100 bases from the cleavage site, it may be possible that other more distal tissue-specific signatures may be present. Alternatively, sequence signatures may not be fully predictive since tissue-specific proteins can act by modulating core polyadenylation proteins instead of directly binding to the transcript (as described, for example, by MacDonald et al., Tissue-specific mechanisms of alternative polyadenylation: testis, brain, and beyond, *Wiley Interdiscip. Rev. RNA*, 2010; which is hereby incorporated by reference in its entirety).

Since an APA model can be used to assess the effects of genetically defined therapies, such as oligonucleotide therapies as described in Example 4, by combining this example with Example 4, the resulting system and method can be used to identify oligonucleotide therapies that act in a tissue-specific manner. In addition, the system and method can be used to identify other genetically defined therapies, such as gene editing and gene therapies.

Example 7—a Convolution Neural Network Model of Polyadenylation to Predict the Effect of Genomic Variations This work begins with a feature-based model, and subsequently a Conv-Net (convolutional neural network) is added for comparison with an expectation of approaching the performance of the Feature-Net, not necessarily surpassing it. Given that the polyadenylation features are derived from many other studies, other approaches of obtaining the feature-based models, which include the logistic regression classifier, are noted. The Conv-Net may learn a better model absent any insights or hypotheses about mechanism. This is surprising at first, but perhaps not so if viewed in the context of other applications of machine learning like computer vision, where hand-crafted features have been largely superseded by models which learn directly from image pixels.

In addition, the Conv-Net has additional advantages that may not be available in feature-based models. For instance, it is completely free to discover novel sequence elements that may be relevant for polyadenylation regulation from data. An example set of filters from the Conv-Net model is shown in Example 12. It also has the potential to be more computationally efficient. Feature extraction from sequences can be the most computational intensive aspect of a model during inference. This is not required for models that directly operate on sequences. There are additional operations that are required in the Conv-Net, but these computations can be significantly sped up by graphics processing units, which can be important for application of the model to entire genomes.

Figure 6:
FIG. 6 illustrates a saliency map from the Cony-Net of a section of oligo-targeted mRNA. Figure discloses SEQ ID NO: 7.

Since the Conv-Net operates directly on the genomic sequence, it also enables one to perform analysis at the single-base resolution more naturally. By analyzing the flow of gradients, the Conv-Net can determine how each base in the input sequence changes the output of the model. If a model requires feature extraction, such as the Feature-Net, the output must be analyzed relative to each feature. Furthermore, in the Feature-Net, many features are derived in discrete sections of the genome (four in this case, as described, for example, in Example 8) to reduce the dimensionality of the input. The Conv-Net on the other hand, is more efficient at sharing model parameters, thereby enabling the motif filters to be applied at much finer spatial steps across a genomic sequence (a stride of 1 is used), while still make overfitting manageable during training. By computing the gradients, analysis regarding the magnitude and direction of the effect of each base on the model's output can be performed. This has the potential to offer a prescription to the design of oligonucleotides for anti-sense therapies. FIG. 6 shows the saliency map of a region of the oligo-targeted mRNA examined in Example 4, which spans the first three polyadenylation signals. This is different from a mutation map approach, which visualizes the change in the model's predictions between the reference genome and mutation at each base for the alternate nucleotides. Here, the gradient of each base relative to the model's prediction is shown, which includes the reference genomic sequence. It is also computed differently, involving a single backpropagation step in the Conv-Net. This operation may not be readily available in the Feature-Net, where the genomic sequence may be separated from the model by a feature extraction pipeline, and therefore dependent on the complexity and choices in the pipeline. This saliency map can be generated for large stretches of the genome to look for potential sensitive regions to alter polyadenylation for therapeutic purposes. Examples of such regions include an oligonucleotide targeted Type 1 Poly(A) signal, a location of a Type 4 Poly(A) signal, and an oligonucleotide Type 2 Poly(A) signal, as shown in FIG. 6.

Regulation of polyadenylation is a crucial step in gene expression, and mutations in DNA elements that control polyadenylation can lead to diseases. Accurate, predictive models of polyadenylation may enable a deeper understanding of the sequence determinants of gene regulation and provide an important new approach to detecting and treating damaging genetic variations. As illustrated by the above examples, the present disclosure provides the polyadenylation code, a versatile model that can predict alternative polyadenylation patterns from transcript sequences and can generalize to multiple tasks that it is not trained on. Beyond its original trained usage to predict PAS selection from competing sites, it can classify variants near PAS and can be used for PAS discovery. Analysis reveals what sequences increase and decrease the strength of a PAS, and features that are associated with tissue-specific and constitutive PAS are identified. Further, the potential of the model to infer, and design for, the effects of antisense oligonucleotide treatment in the 3'-UTR is demonstrated.

Since an APA model can be used to assess the effects of genetically defined therapies, such as oligonucleotide therapies as described in Example 4, by combining this example with Example 4, the resulting convolutional neural network-based system and method can be used to identify oligonucleotide therapies that act in a tissue-specific manner. In addition, the convolutional neural network-based system and method can be used to identify other genetically defined therapies, such as gene editing and gene therapies.

Example 8—Feature Description of the Feature-Net

Figure 7:
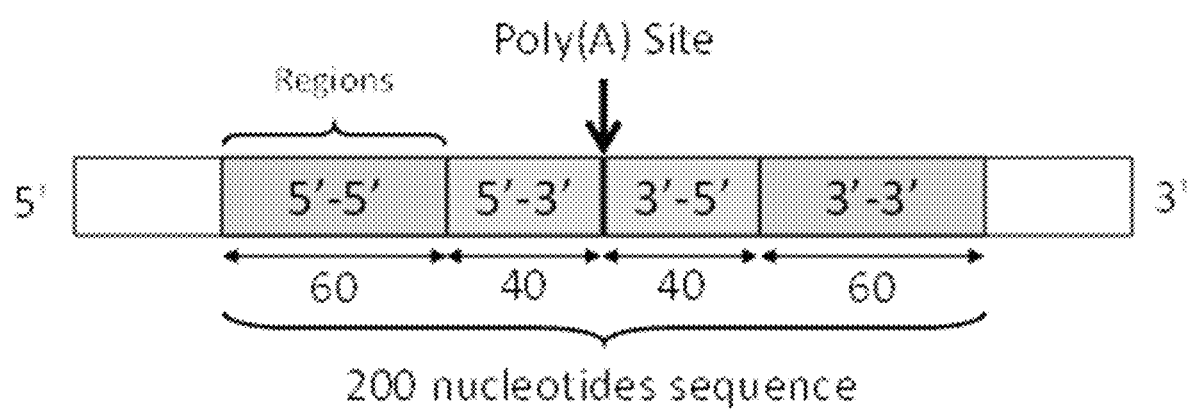
FIG. 7 illustrates regions around a polyadenylation site where features are extracted.

FIG. 7 illustrates regions around a polyadenylation site where features are extracted. For example, a given sequence comprising 200 nucleotides may include four different regions (a 5'-5' region which is 60 nucleotides in length, a 5'-3' region which is 40 nucleotides in length, a 3'-5' region which is 40 nucleotides in length, and a 3'-3' region which is 60 nucleotides in length) such that a Poly(A) site is found in between the 5'-3' and the 3'-5' regions. Table 6 illustrates examples of feature groups and corresponding regions and number of features. A "*" indicates redundant features that are present in multiple feature groups, which are removed.

TABLE 6

Examples of feature groups and corresponding regions and number of features.

| Feature Group* | Regions | # Features |
|---|---|---|
| Poly(A) Signal[1] | 5'-5' | 26 |
|  | 5'-3' | 26 |
| AUE Elements[2] | 5'-5' | 12 |
| CUE Elements[2] | 5'-3' | 2 |
| CDE Elements[2] | 3'-5' | 15 |
| ADE Elements[2] | 3'-3' | 12 |
| RBP Motifs[3] | All 4 | 18 × 4 |
| 1-mers | All 4 | 4 × 4 |
| 2-mers | All 4 | 16 × 4 |
| 3-mers | All 4 | 64 × 4 |
| 4-mers | All 4 | 248 × 4 |
| Mean and Max Nucleosome Occupancy | 5' of PAS 3' of PAS Full Seq | 12 |
| Position | — | 1 |

[1]Polyadenylation Signals (as described, for example, by Tian et al., A large-scale analysis of mRNA polyadenylation of human and mouse genes, *Nucleic Acids Res.*, 2005; by Beaudoing et al., Patterns of variant polyadenylation signal usage in human genes, *Genome Res.*, 2000; by Ni et al., Distinct polyadenylation landscapes of diverse human tissues revealed by a modified PA-seq strategy. *BMC Genomics*, 2013; and by Derti et al., A quantitative atlas of polyadenylation in five mammals, *Genome Res*, 2012; each of which is hereby incorporated by reference in its entirety), including the following:

AATAAA, ATTAAA, TATAAA, AGTAAA,

AAGAAA, AATATA, AATACA, CATAAA,

GATAAA, AATGAA, TTTAAA, ACTAAA,

AATAGA, AAAAAG, AAAATA, GGGGCT,

AAAAAA, ATAAAA, AAATAA, ATAAAT,

TTTTTT, ATAAAG, TAAAAA, CAATAA,

TAATAA, ATAAAC

[2]Cis-Elements (as described, for example, in Table 1 by Hu et al., Bioinformatic identification of candidate cis-regulatory elements involved in human mRNA polyadenylation, *RNA*; which is hereby incorporated by reference in its entirety).

[3]RNA Binding Motifs, in IUPAC notation: CPEB1: UUUUAU, hnRNP-H1: GGGAGG, hnRNP-H2: GGAGGG, MBNL_v1: GCUUGC, MBNL_v2: YGCY, MBNL_v3: YGCUKY, PABPN1: ARAAGA, PTBP1: UUUUCU, NOVA: UCAY, PCBP1: CCWWHCC, PCBP2: CCYYCCH, ESRP2: UGGGRAD, hnRNP-F/H_v1: GGGA, hnRNP-F/H_v2: UKKGGK, hnRNP-F/H_v3: GGSKG, CFIm: UGUA, CstF-64: UGUGU, SRSF1: GAAGAA Since an APA model can be used to assess the effects of genetically defined therapies, such as oligonucleotide therapies as described in Example 4, by combining this example with Example 4, the resulting system and method can be used to identify the features, such as RNA-protein binding motifs and nucleosome occupancies, that contribute to the effectiveness of oligonucleotide therapies. In addition, the system and method can be applied to other genetically defined therapies, such as gene editing and gene therapies.

Example 9—Variants Near Polyadenylation Sites Extracted from ClinVar

Examples of variants are given below in notation chromosome:position:reference:variant, based on the hg19 assembly.

Pathogenic (CLNSIG = 5):

chr1:11082794:T:C, chr8:22058957:T:C, chr11:2181023:T:C,
chr11:5246715:T:C, chr11:5246716:T:A, chr11:5246716:T:C,
chr11:5246717:T:C, chr11:5246718:A:G, chr11:5246718:A:T,
chr11:46761055:G:A, chr16:223691:A:G, chr22:51063477:T:C Benign (CLNSIG = 2):

chr1:156109644:G:A, chr1:197053394:G:A, chr2:71004492:T:C,
chr2:166847735:T:A, chr2:166847735:T:C, chr2:179326003:A:C,
chr2:207656535:T:C, chr3:178952181:T:C, chr4:141471538:C:T,
chr4:187131799:T:C, chr5:112180071:A:G, chr5:118877695:A:G,
chr6:7586120:T:A, chr6:116953612:A:G, chr6:158532382:T:C,
chr10:27035405:A:G, chr11:74168280:G:A, chr11:77811990:T:C,
chr12:64202890:C:G, chr16:15797843:G:C, chr18:48604848:C:T,
chr18:52895244:C:T, chr19:1226654:C:T, chr19:1395497:C:T,
chr19:1395500:C:A, chr19:1395500:C:T, chr19:1395503:C:T,
chr19:4090577:G:A, chr19:4090588:G:A, chr19:36494234:A:G,
chr19:36595935:G:A, chr19:50364490:G:A, chr22:29083867:G:A,
chr22:50964189:C:T, chr22:50964196:G:A, chr22:50964196:G:T,
chrX:135126891:A:T, chrX:153287318:G:C, chrX:153294581:A:G,
chrX:153294684:C:T, chrX:153294987:C:G, chrX:153295012:C:T,
chrX:153295725:C:C, chrX:153295726:G:A, chrX:153295763:G:C,
chrX:153295782:C:G, chrX:153295809:C:T, chrX:153295810:G:A

Example 10—Sample Predicted Polyadenylation Track

Figure 8:
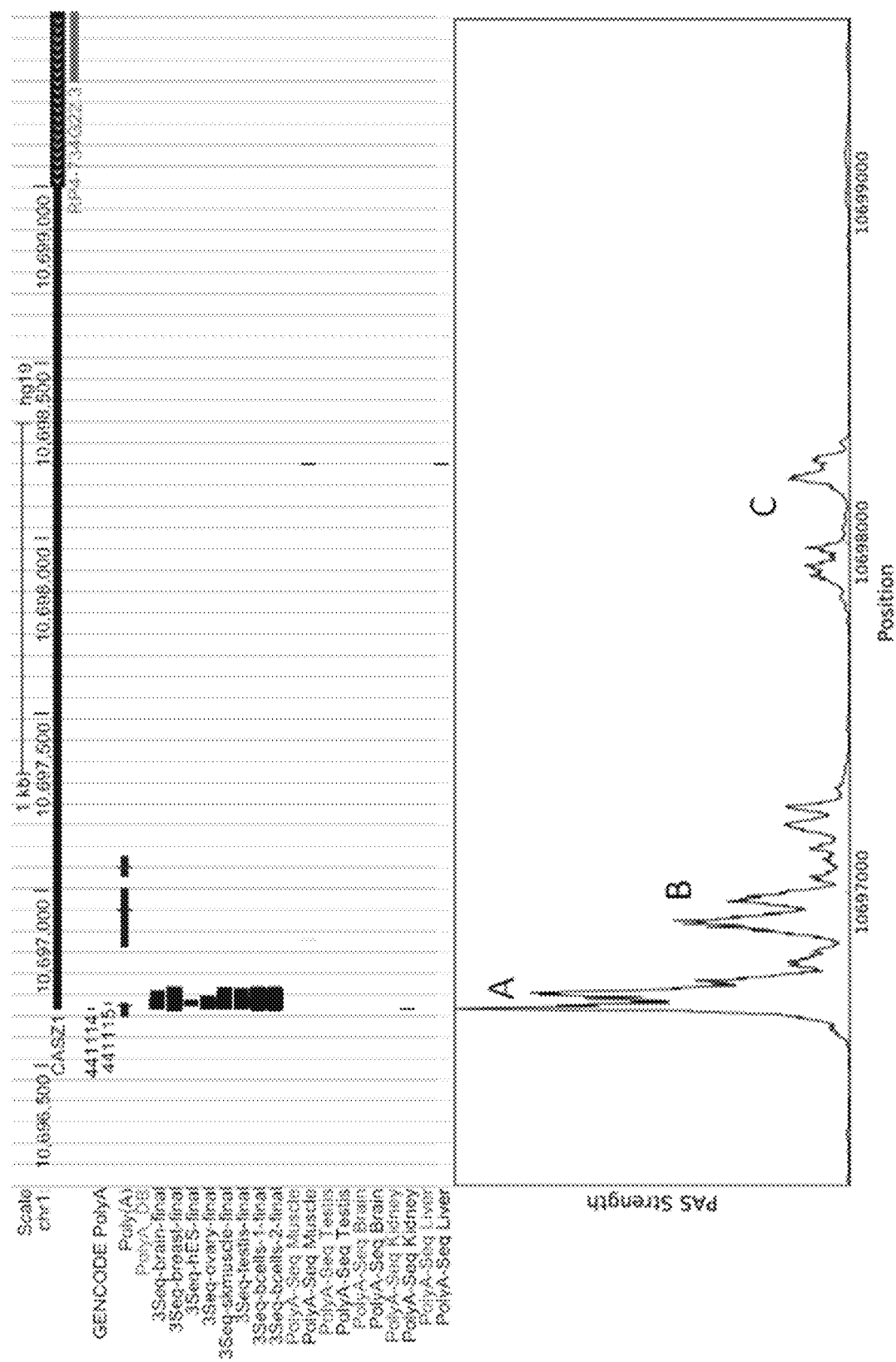
FIG. 8 illustrates an example application of scanning the Conv-Net model across a section of the human genome to identify potential polyadenylation sites.

FIG. 8 illustrates an example application of scanning the Conv-Net model across a section of the human genome to identify potential polyadenylation sites. At the top of FIG. 8, a snapshot is shown from the UCSC genome browser, showing tracks from top to bottom: GENCODE gene annotations, GENCODE Poly(A) track, predicted and reported PAS from polyA_DB (as described, for example, by Cheng et al. and by Zhang et al., PolyA_DB: a database for mammalian mRNA polyadenylation, *Nucleic Acids Res.*, 2005; which is hereby incorporated by reference in its entirety), 3'-Seq (as described, for example, by Lianoglou et al., Ubiquitously transcribed genes use alternative polyadenylation to achieve tissue-specific expression, *Genes Dev.*, 2013; which is hereby incorporated by reference in its entirety), and PolyA-Seq (forward and reverse strands) (as described, for example, by Derti et al., A quantitative atlas of polyadenylation in five mammals, *Genome Res.*, 2012; which is hereby incorporated by reference in its entirety). At the bottom of FIG. 8, predictions from the model are shown.

Figure 9:
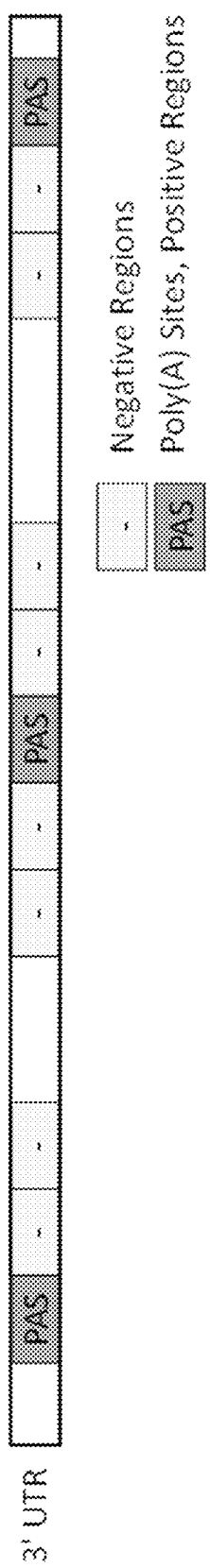
FIG. 9 illustrates positive and negative regions for PAS discovery evaluation.

Example 11—Definition of Positive and Negative Regions for PAS Discovery Evaluation FIG. 9 illustrates positive and negative regions for PAS discovery evaluation. Two regions immediately adjacent to each polyadenylation site (PAS) are defined as negatives for classification. This ensures that the negatives have similar nucleotide composition compared to the positive sequences. Regions that are not between existing PAS are excluded to avoid including terminal exonic regions. If the spacing between adjacent PAS cannot fit four negative regions, they are also excluded from the negative set.

Example 12—Example Filters Learned by the Convolutional Neural Network

Figure 10:
FIG. 10 illustrates example filters learned by a convolutional neural network.

FIG. 10 illustrates example filters learned by a convolutional neural network. Specifically, an example set of the 80 filters that are learned by the Conv-Net are shown (numbered from 0 to 79). All filters are mean-subtracted and plotted with the same scale (i.e., the max and min for each filter plot is the same). Different shades or colors can be used to denote positive and negative values. Various filters are blank, suggesting the number of filters in the Conv-Net model can be reduced. A filter that detects the two most common polyadenylation signal motifs, ATTAAA and AATAAA can be seen in filter #23, which is followed by a strong avoidance of a T nucleotide. Filters resembling GU-rich elements, such as filter #4 can also be found.

Example 13—Model Hyperparameters

Table 7 illustrates examples of hyperparameters for three different models: a logistic regression (LR), the Feature-Net, and the Conv-Net. The following hyperparameters are determined by random sampling and selecting the set that provide the best validation performance. The range each hyperparameter is sampled from is indicated. The number of training epochs is fixed to 50.

TABLE 7

Examples of hyperparameters for logistic regression (LR), Feature-Net, and Conv-Net.

| Hyperparameter | LR | Feature-Net | Conv-Net |
|---|---|---|---|
| Mini-batch size [50 to 2500] | 1777 | 1520 | 2042 |
| Hidden units in the final fully connected layer per tissue [10 to 2000] | — | 1384 | 119 |
| Learning rate [0.0001 to 0.5] | 0.10066 | 0.09537 | 0.35714 |
| Initial momentum [0 to 0.99] | 0.29108 | 0.21876 | 0.43301 |
| L1 decay [1e-8 to 5e-3] | 0.000087 | 0.000177 | 0.000181 |
| Hidden units in the first hidden layer [50 to 2500] | — | 1244 | — |
| Number of filters [80 or 96] | — | — | 80 |
| Filter width [9 or 12] | — | — | 12 |
| Filter stride [fixed] | — | — | 1 |
| Pool width [fixed] | — | — | 20 |
| Pool stride [fixed] | — | — | 10 |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for administering an antisense oligonucleotide to a subject, the method comprising:
   (a) providing a plurality of genomic sequences, wherein the plurality of genomic sequences comprises (1) a reference sequence and (2) a variant sequence obtained by computer processing the reference sequence based at least in part on the antisense oligonucleotide, wherein the reference sequence is (i) derived from a human genome, (ii) obtained by sequencing deoxyribonucleic acid (DNA) or ribonucleic acid (RNA) of a bodily sample obtained or derived from the subject, or (iii) a genetic aberration thereof, and wherein the antisense oligonucleotide is complementary to at least a portion of the reference sequence;
   (b) for each of the plurality of genomic sequences:
      i. identifying a plurality of candidate polyadenylation sites in the genomic sequence;
      ii. extracting a polyadenylation feature vector for each of the plurality of candidate polyadenylation sites, wherein each of the polyadenylation feature vectors comprises a set of features determined based at least in part on a set of nucleotides in the genomic sequence; and
      iii. applying a trained algorithm to the plurality of polyadenylation feature vectors to determine a set of preferences $p_1, p_2, \ldots, p_n$ for the plurality of candidate polyadenylation sites;
   (c) computer processing the plurality of sets of preferences for each of the plurality of genomic sequences with each other to determine an effect of the antisense oligonucleotide on the plurality of candidate ployadenylation sites; and
   (d) administering a therapeutically effective amount of the antisense oligonucleotide, wherein the administered therapeutically effective amount of the antisense oligonucleotide modulates polyadenylation of at least one of the plurality of candidate polyadenylation sites in the subject.

2. The method of claim 1, wherein calculating determining the set of preferences for each of the plurality of genomic sequences comprises:
   for each of the plurality of candidate polyadenylation sites, computer processing the plurality of polyadenylation feature vectors of the genomic sequence to determine an intermediate representation $r_i$ for an ith candidate polyadenylation site, the intermediate representation comprising a numerical value; and
   computer processing the set of intermediate representations $r_1, r_2, \ldots, r_n$ for the plurality of candidate polyadenylation sites to determine the set of preferences $p_1, p_2, \ldots, p_n$ corresponding to the plurality of candidate polyadenylation sites.

3. The method of claim 2, wherein computer processing the plurality of polyadenylation feature vectors comprises using a convolutional neural network, to process the plurality of polyadenylation feature vectors to generate the set of intermediate representations $r_1, r_2, \ldots, r_n$ for the plurality of candidate polyadenylation sites.

4. The method of claim 2, wherein the intermediate representation for the ith candidate polyadenylation site comprises a numerical value $r_i$, and wherein computer processing the set of intermediate representations comprises applying a softmax function to the set of intermediate representations $r_1, r_2, \ldots, r_n$ for the plurality of candidate polyadenylation sites to determine the set of preferences $p_1, p_2, \ldots, p_n$ for the plurality of candidate polyadenylation sites.

5. The method of claim 2, wherein the intermediate representation for the ith candidate polyadenylation site comprises a numerical value $r_i$, and wherein computer processing the set of intermediate representation comprises determining each preference $p_i$ of the set of preferences as $$p_i = \frac{\exp(r_i)}{\exp(r_1) + \exp(r_2) + \ldots + \exp(r_n)},$$

wherein exp is an exponential function or a numerical approximation of an exponential function.

6. The method of claim 2, wherein computer processing the set of intermediate representations comprises determining each preference $p_i$ of the set of preferences as $$p_i = \frac{relu(r_i)}{relu(r_1) + relu(r_2) + \ldots + relu(r_n)},$$

wherein relu is a rectified linear function.

7. The method of claim 2, wherein computer processing the set of intermediate representations comprises determining each preference $p_i$ of the set of preferences as $$p_i = \frac{m(r_i)}{m(r_1) + m(r_2) + \ldots + m(r_n)},$$

wherein m( ) is a non-negative monotonic function.

8. The method of claim 1, wherein the genetic aberration comprises a single nucleotide variant (SNV) or an insertion or deletion (indel).

9. The method of claim 1, wherein at least one of the set of nucleotides is located within about 100 nucleotides of a location in the genomic sequence of the candidate polyadenylation site.

10. The method of claim 1, wherein each of the plurality of polyadenylation feature vectors comprises one or more of:
   (a) a subsequence of the genomic sequence encoded using a 1-of-4 binary vector for a nucleotide selected from adenine (A), thymine (T), cytosine (C), and guanine (G);

(b) a subsequence of the genomic sequence encoded using a 1-of-4 binary vector for a nucleotide selected from adenine (A), uracil (U), cytosine (C), and guanine (G);
(c) a set of binary components;
(d) a set of categorical components;
(e) a set of integer components; and
(f) a set of real-valued components.

11. The method of claim 10, wherein at least one of the set of binary components comprises a value indicative of the presence of a cleavage factor sequence in the candidate polyadenylation site, or a value indicative of the absence of a cleavage factor sequence in the candidate polyadenylation site.

12. The method of claim 10, wherein at least one of the set of binary components comprises a value indicative of the presence of a cleavage factor sequence adjacent to the candidate polyadenylation site or a value indicative of the absence of a cleavage factor sequence adjacent to the candidate polyadenylation site.

13. The method of claim 10, wherein the at least one of the plurality of polyadenylation feature vectors comprises a feature selected from the group consisting of:
 a PolyA signal AAUAAA in a 5'-3' region,
 a log distance between the candidate polyadenylation site and a nearest different candidate polyadenylation site among the plurality of candidate polyadenylation sites,
 a PolyA AUUAAA in a 5'-3' region,
 a 1-mer C in a 5'-3' region,
 a 1-mer U in a 5'-3' region,
 a 2-mer AG in a 5'-3' region,
 a 2-mer CA in a 3'-5' region,
 a 3-mer AAA in a 3'-5' region,
 a 3-mer UGU in a 5'-3' region,
 a 3-mer UGU in a 5'-3' region,
 a 4-mer AAAA in a 3'-5' region,
 a cleavage factor Im UGUA in a 5'-5' region,
 a PolyA signal CAAUAA in a 5'-3' region,
 a PolyA signal AUAAAG in a 5'-3' region, and
 a PolyA signal AGUAAA in a 5'-5' region.

14. The method of claim 10, wherein at least one of the set of real-valued components comprises a log distance, in number of nucleotides in the genomic sequence, from (1) the candidate polyadenylation site to (2) a nearest different candidate polyadenylation site among the plurality of candidate polyadenylation sites.

15. The method of claim 1, further comprising, for at least one of the plurality of genomic sequences, identifying a maximally preferred candidate polyadenylation site among the plurality of candidate polyadenylation sites, wherein the maximally preferred candidate polyadenylation site has a largest numerical value $p_{max}$, among the set of preferences $p_1, p_2, \ldots, p_n$.

16. The method of claim 1, wherein determining the set of preferences comprises:
 providing a set of numerical parameters; and
 determining a multiplication product comprising at least one feature from at least one of the plurality of polyadenylation feature vectors and at least one numerical parameter of the set of numerical parameters.

17. The method of claim 16, further comprising applying a machine learning algorithm to the plurality of polyadenylation feature vectors to determine the set of preferences, the machine learning algorithm comprising adjusting a numerical parameter of the set of numerical parameters to decrease a loss function.

18. The method of claim 17, wherein adjusting the numerical parameter of the set of numerical parameters comprises performing a gradient-based learning procedure.

19. The method of claim 18, wherein the gradient-based learning procedure comprises stochastic gradient descent.

20. The method of claim 17, wherein the loss function comprises a cross entropy function.

21. The method of claim 1, wherein each preference $p_i$ among the set of preferences $p_1, p_2, \ldots, p_n$ indicates a probability of selection of an ith candidate polyadenylation site among the plurality of candidate polyadenylation sites.

22. The method of claim 1, wherein a one-to-one correspondence exists between one or more of the plurality of candidate polyadenylation sites of the reference sequence and one or more of the plurality of candidate polyadenylation sites of the variant sequence, and wherein processing the plurality of sets of preferences comprises comparing each of at least one preference in the set of preferences of the reference sequence to the corresponding preference in the set of preferences of the variant sequence which is in one-to-one correspondence.

23. The method of claim 22, wherein (c) further comprises calculating a set of changes in preference $\Delta p_1, \Delta p_2, \ldots, \Delta p_n$ corresponding to the plurality of candidate polyadenylation sites of the reference sequence and the plurality of candidate polyadenylation sites of the variant sequence to determine the effect of the antisense oligonucleotide.

24. The method of claim 1, wherein the variant sequence obtained by computer processing the reference sequence based on the antisense oligonucleotide, is obtained by replacing one or more nucleotides of the at least the portion of the reference sequence with an N base, a uniform weighting of the 4 bases, or randomly selected bases.

25. The method of claim 1, comprising applying the trained algorithm to a plurality of polyadenylation feature vectors indicative of a relative positioning of the plurality of candidate polyadenylation sites to determine the set of preferences.

26. The method of claim 1, wherein the determined effect of the antisense oligonucleotide comprises a decreased preference for one or more of the plurality of candidate polyadenylation sites.

27. The method of claim 1, wherein the determined effect of the antisense oligonucleotide comprises an increased preference for one or more of the plurality of candidate polyadenylation sites.

28. The method of claim 1, wherein the antisense oligonucleotide has a length of about 10 to about 50 nucleotides.

29. The method of claim 1, further comprising determining a tissue-specific effect of the antisense oligonucleotide based at least in part on whether a plurality of polyadenylation feature vectors of the plurality of candidate polyadenylation sites comprises tissue-specific polyadenylation features.

30. The method of claim 29, wherein the tissue-specific polyadenylation features comprise a feature selected from the group consisting of:
 a 4-mer UUGU in a 5'-5' region,
 a 3-mer UUG in a 3'-3' region,
 a 4-mer CCCC in a 3'-3' region,
 a 3-mer, UGU in a 5'-5' region,
 a 4-mer, UCCC in a 3'-3' region,
 a 4-mer, CGGC in a 5'-3' region,
 a cis-element UUUGUA in a 5'-5' region,
 a cleavage factor Im UGUA in a 5'-5' region,
 a 3-mer, UUG in a 5'-5' region,
 a 3-mer, AUC in a 5'-5' region, a 3-mer, UCC in a 3'-3' region,
a 2-mer, UC in a 5'-5' region,
a 4-mer, AUCC in a 5'-5' region,
a 2-mer, UU in a 5'-5' region, and
a 3-mer CCU in a 3'-3' region.

* * * * *

UNITED STATES PATENT AND TRADEMARK OFFICE
CERTIFICATE OF CORRECTION

PATENT NO. : 11,322,225 B2
APPLICATION NO. : 17/162224
DATED : May 3, 2022
INVENTOR(S) : Brendan Frey and Michael Ka Kit Leung It is certified that error appears in the above-identified patent and that said Letters Patent is hereby corrected as shown below:

In the Claims

Claim 1, Line 31:
Replace "oligonucleotide on the plurality of candidate ployade-" with --oligonucleotide on the plurality of candidate polyade- --.

Claim 1, Line 33:
Replace "(d) administering a therapeutically effective amount of the" with --(d) administering a therapeutically effective amount of the antisense oligonucleotide to the subject based at least in part on the determined effect of the--.

Claim 2, Line 1:
Replace "2. The method of claim 1, wherein calculating determin-" with --2. The method of claim 1, wherein determin- --.

Claim 3, Line 3:
Replace "using a convolutional neural network, to process the plural-" with --using a convolutional neural network to process the plural- --.

Claim 13, Line 8:
Replace "a PolyA AUUAAA in a 5'-3' region," with --a PolyA signal AUUAAA in a 5'-3' region,--.

Claim 13, Line 15:
Replace "a 3-mer UGU in a 5'-3' region" with --a 3-mer UGU in a 5'-5' region--.

Signed and Sealed this
Sixteenth Day of May, 2023

Katherine Kelly Vidal
*Director of the United States Patent and Trademark Office*

SEQUENCE LISTING

<160> NUMBER OF SEQ ID NOS: 7

<210> SEQ ID NO 1
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1
gcagcuguuu cg                                                    12

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gagaattaac aaga                                                  14

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggtctgcacg aatca                                                 15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cacaattttc aagaa                                                 15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgtcagaaag aatca                                                 15

<210> SEQ ID NO 6
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
taatttaaat acatcattgc aatgaaaata aatgtttttt attaggcaga atccagatgc     60
tcaaggccct tcataatatc ccccagttta gtagttggac                          100

<210> SEQ ID NO 7
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
tagcaaggca tgatgttaac cagaataaag ttctgagtgt ttttactaca gttgtttttt    60
gaaaacatgg tagaattgga gagtaaaaac tgaatggaag gtttgtatat tgtcagatat   120
tttttcagaa atatgtggtt tccacgatga aaaacttcca tgaggccaaa cgttttgaac   180
taataaaagc ataaatgcaa                                                200
```